United States Patent
Beger et al.

(10) Patent No.: US 8,974,498 B2
(45) Date of Patent: Mar. 10, 2015

(54) SPINAL COLUMN STABILIZATION SYSTEM AND SURGICAL DEVICE FOR TEMPORARILY STIFFENING A FLEXIBLE INTERMEDIATE SECTION OF A CONNECTING ELEMENT OF THE SPINAL COLUMN STABILIZATION SYSTEM

(71) Applicants: Jens Beger, Tuttlingen (DE); Fabian Hoefer, Tuttlingen (DE); Sven Krueger, Trossingen (DE)

(72) Inventors: Jens Beger, Tuttlingen (DE); Fabian Hoefer, Tuttlingen (DE); Sven Krueger, Trossingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 13/790,843

(22) Filed: Mar. 8, 2013

(65) Prior Publication Data

US 2013/0211454 A1 Aug. 15, 2013

Related U.S. Application Data

(63) Continuation of application No. PCT/EP2011/066164, filed on Sep. 19, 2011.

(30) Foreign Application Priority Data

Sep. 20, 2010 (DE) .......................... 10 2010 037 666
Oct. 21, 2010 (DE) .......................... 10 2010 060 101

(51) Int. Cl.
*A61B 17/70* (2006.01)
*A61B 17/00* (2006.01)

(52) U.S. Cl.
CPC .............. *A61B 17/70* (2013.01); *A61B 17/701* (2013.01); *A61B 17/7011* (2013.01);
(Continued)

(58) Field of Classification Search
USPC ................. 606/60, 246–279, 86 A, 86 B, 99; 81/340, 419, 421–426.5; 140/106
See application file for complete search history.

(56) References Cited

U.S. PATENT DOCUMENTS 273,382 A * 3/1883 Packham .................... 72/409.19
1,268,922 A * 6/1918 Bryan .......................... 72/390.5
(Continued)

FOREIGN PATENT DOCUMENTS

DE  102005061368 B3  7/2007
DE  102007047908 A1  7/2008
(Continued)

OTHER PUBLICATIONS

International Search Report for International Application Serial No. PCT/EP2011/066164 dated Jan. 25, 2012, with English language description of category codes, 6 pgs.
(Continued)

*Primary Examiner* — Eduardo C Robert
*Assistant Examiner* — Jacqueline Johanas
(74) *Attorney, Agent, or Firm* — RatnerPrestia

(57) ABSTRACT

A surgical device is used for temporarily stiffening an at least partially flexible intermediate section of a connecting element for a spinal column stabilization system. The connecting element includes a first attachment section for fixing to a first bone fixation device and a second attachment section for fixing to a second bone fixation device. The at least partially flexible intermediate section is arranged between the first and second attachment sections. The intermediate section defines at least one recess configured to enable deformation of the intermediate section. The surgical device includes at least one blocking element which is adapted to be brought into engagement with the intermediate section at least partially with a positively locking connection for temporarily preventing deformation of the flexible intermediate section. An improved spinal column stabilization system includes at least one first bone fixation device, at least one second bone fixation device and a connecting element.

18 Claims, 22 Drawing Sheets

(52) U.S. Cl.
CPC ........ *A61B 17/7026* (2013.01); *A61B 17/7028* (2013.01); *A61B 17/7083* (2013.01); *A61B 17/7004* (2013.01); *A61B 2017/00004* (2013.01)
USPC ...................................... 606/255; 606/86 A

(56) References Cited

U.S. PATENT DOCUMENTS

| | | | |
|---|---|---|---|
| 1,824,219 A * | 9/1931 | Loveless | 140/106 |
| 3,094,151 A * | 6/1963 | Dugger | 140/106 |
| 3,808,870 A * | 5/1974 | Blancett | 72/413 |
| 3,918,472 A * | 11/1975 | Brown | 140/106 |
| 4,043,174 A * | 8/1977 | Paolino | 72/412 |
| 4,049,268 A * | 9/1977 | Ray | 473/557 |
| D250,451 S * | 12/1978 | Chartier et al. | D8/52 |
| 4,283,933 A * | 8/1981 | Wiener | 72/409.12 |
| 5,063,770 A * | 11/1991 | Chen | 72/409.11 |
| 5,084,935 A * | 2/1992 | Kalthoff | 7/132 |
| 5,364,397 A * | 11/1994 | Hayes et al. | 606/86 A |
| 5,415,659 A * | 5/1995 | Lee et al. | 606/276 |
| 6,395,033 B1 * | 5/2002 | Pepper | 623/17.13 |
| 6,776,615 B2 * | 8/2004 | Dietrich | 433/159 |
| 7,090,679 B2 * | 8/2006 | Saint-Martin et al. | 606/99 |
| 7,285,121 B2 * | 10/2007 | Braun et al. | 606/279 |
| 7,473,257 B2 * | 1/2009 | Knopfle et al. | 606/101 |
| 7,637,185 B2 * | 12/2009 | Montgomery et al. | 81/426 |
| 7,922,750 B2 | 4/2011 | Trautwein | |
| 8,048,114 B2 * | 11/2011 | Tornier | 606/246 |
| 8,197,516 B2 * | 6/2012 | Biyani | 606/250 |
| 2003/0208203 A1 * | 11/2003 | Lim et al. | 606/61 |
| 2005/0203511 A1 * | 9/2005 | Wilson-MacDonald et al. | 606/61 |
| 2006/0030860 A1 * | 2/2006 | Peterman | 606/99 |
| 2006/0166535 A1 * | 7/2006 | Brumfield et al. | 439/179 |
| 2006/0184171 A1 | 8/2006 | Biedermann et al. | |
| 2006/0229608 A1 * | 10/2006 | Foster et al. | 606/61 |
| 2006/0247630 A1 * | 11/2006 | Iott et al. | 606/61 |
| 2007/0078461 A1 * | 4/2007 | Shluzas | 606/61 |
| 2007/0088359 A1 | 4/2007 | Woods | |
| 2007/0167091 A1 | 7/2007 | Schumacher | |
| 2007/0191832 A1 | 8/2007 | Trieu | |
| 2007/0276380 A1 | 11/2007 | Jahng | |
| 2008/0119862 A1 | 5/2008 | Wicker | |
| 2008/0125788 A1 * | 5/2008 | Cohen et al. | 606/104 |
| 2008/0133016 A1 * | 6/2008 | Heinz | 623/17.16 |
| 2008/0228225 A1 | 9/2008 | Trautwein | |
| 2008/0234736 A1 | 9/2008 | Trieu et al. | |
| 2008/0234747 A1 | 9/2008 | Allard | |
| 2008/0300631 A1 * | 12/2008 | Tornier | 606/246 |
| 2009/0118767 A1 | 5/2009 | Hestad | |
| 2009/0228044 A1 | 9/2009 | Jeon | |
| 2010/0004689 A1 * | 1/2010 | Biyani | 606/250 |
| 2010/0222784 A1 * | 9/2010 | Schwab et al. | 606/99 |
| 2010/0331901 A1 * | 12/2010 | Iott et al. | 606/86 A |
| 2011/0040330 A1 * | 2/2011 | Sheffer | 606/249 |
| 2011/0190819 A1 | 8/2011 | Trautwein | |
| 2012/0071927 A1 * | 3/2012 | Beger et al. | 606/255 |
| 2013/0035725 A1 * | 2/2013 | Beger et al. | 606/278 |

FOREIGN PATENT DOCUMENTS

| | | | |
|---|---|---|---|
| DE | 1 02010 000 339.5 | * | 2/2010 |
| WO | WO-2007090015 A1 | | 8/2007 |
| WO | WO-2008073830 A1 | | 6/2008 |
| WO | WO-2008106303 A1 | | 9/2008 |
| WO | WO-2010028165 A1 | | 3/2010 |

OTHER PUBLICATIONS

Office Action for U.S. Appl. No. 13/568,739, dated Aug. 22, 2014.

* cited by examiner

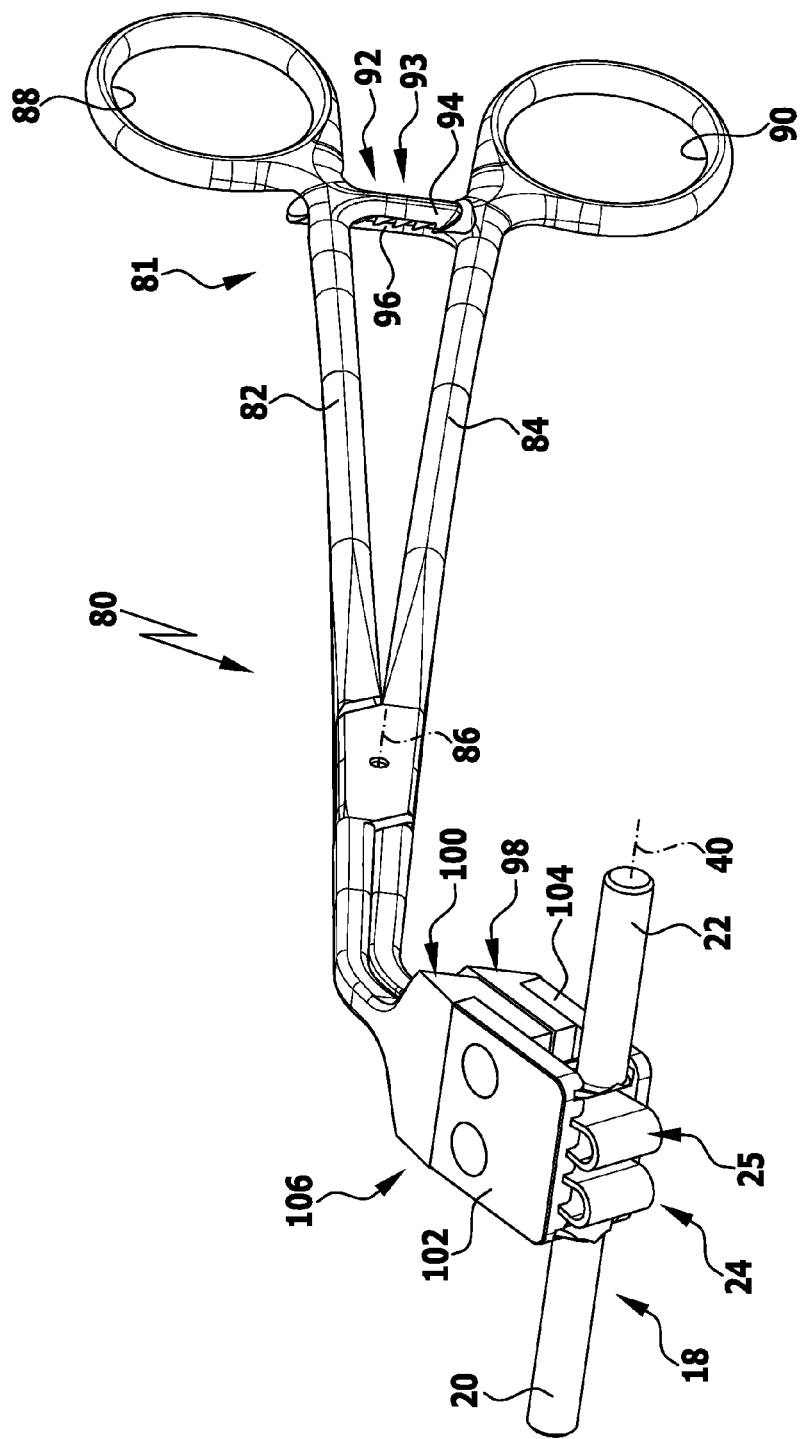

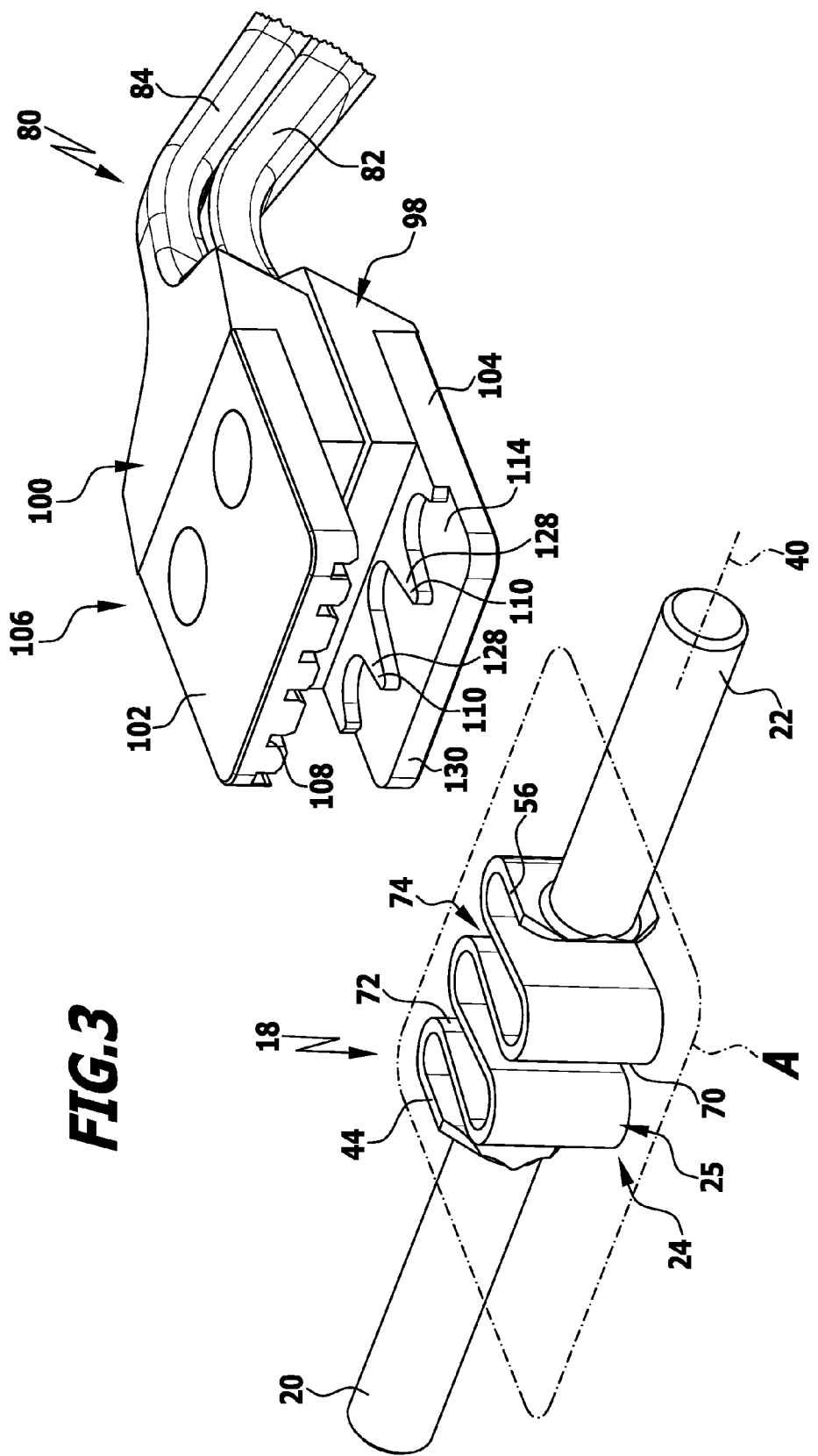

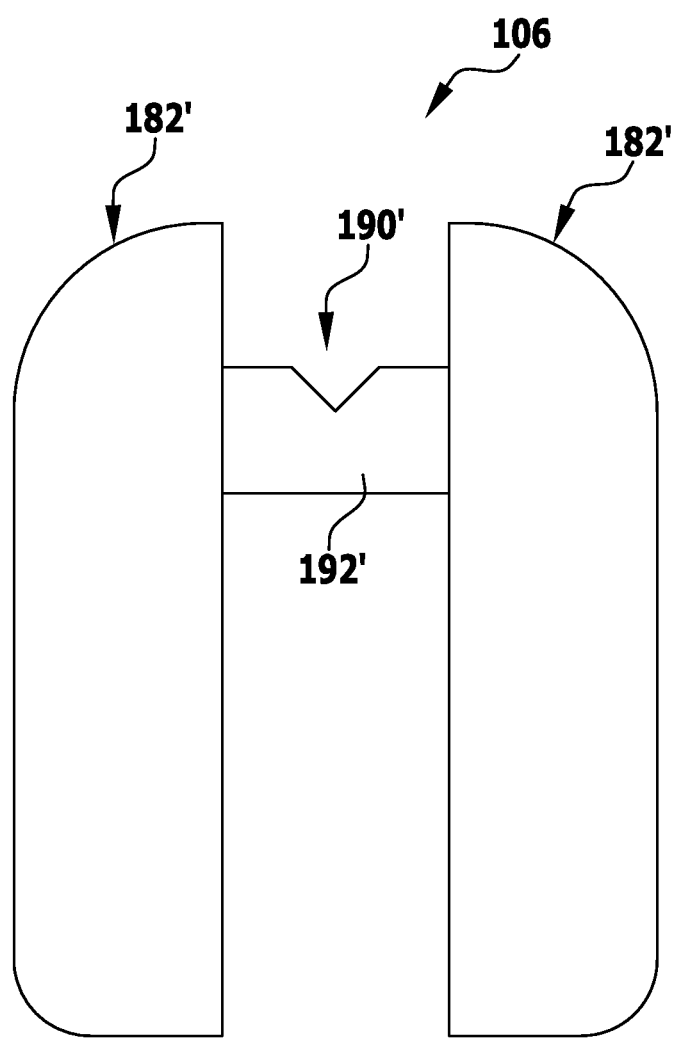

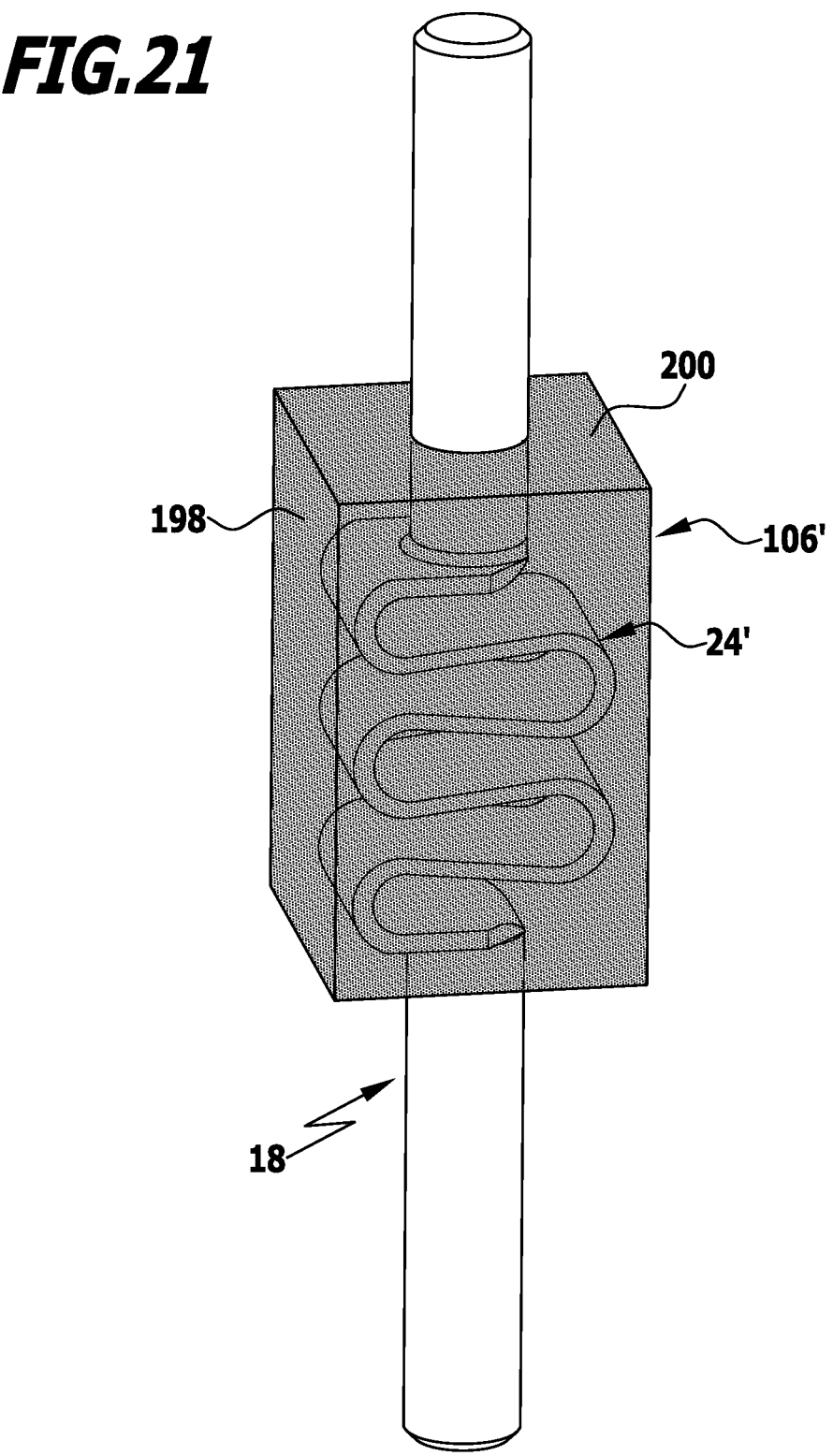

SPINAL COLUMN STABILIZATION SYSTEM AND SURGICAL DEVICE FOR TEMPORARILY STIFFENING A FLEXIBLE INTERMEDIATE SECTION OF A CONNECTING ELEMENT OF THE SPINAL COLUMN STABILIZATION SYSTEM

RELATED APPLICATIONS

This application is a continuation of International Application no. PCT/EP2011/066164, filed Sep. 19, 2011, which claims the benefit of priority of German Patent Application no. 10 2010 037 666.3, filed Sep. 20, 2010, and German Patent Application no. 10 2010 060 101.2, filed Oct. 21, 2010. The contents of all of the foregoing applications in this paragraph are incorporated by reference in their entirety and for all purposes.

FIELD OF THE INVENTION

The present invention relates to surgical devices for temporarily stiffening an at least partially flexible intermediate section of a connecting element for a spinal column stabilization system generally, and more specifically to a surgical device for temporarily stiffening an at least partially flexible intermediate section of a connecting element for a spinal column stabilization system, the connecting element comprising a first attachment section for fixing to a first bone fixation device, a second attachment section for fixing to a second bone fixation device, and the at least partially flexible intermediate section arranged or formed between the first and second attachment sections, the intermediate section defining at least one recess which is configured so as to enable deformation of the intermediate section.

The present invention further relates to spinal column stabilization systems generally, and more specifically to a spinal column stabilization system comprising at least one first bone fixation device, at least one second bone fixation device and a connecting element, the connecting element comprising a first attachment section for fixing to a first bone fixation device, a second attachment section for fixing to a second bone fixation device, and an at least partially flexible intermediate section arranged or formed between the first and second attachment sections, the intermediate section defining at least one recess which is configured so as to enable deformation of the intermediate section.

BACKGROUND

A spinal column stabilization system of the kind described at the outset, in particular, with a connecting element, which comprises two attachment sections and a flexible intermediate section arranged between these is known, for example, from US 2005/0184171 A1. Owing to the at least partially flexible intermediate section, the connecting element may become deformed in an undesired manner during the implantation. This risk exists particularly when introducing and locking the rod to corresponding bone fixation devices, for example, to bone screws in the form of pedicle screws.

A surgical instrument which may be used for temporarily stiffening the flexible intermediate section is known, for example, from US 2008/0119852 A1. However, this instrument is not explicitly provided for the intended use and owing to its design is rather unsuitable for practical application.

SUMMARY

In a first aspect of the invention, a surgical device for temporarily stiffening an at least partially flexible intermediate section of a connecting element for a spinal column stabilization system is provided. Said connecting element comprises a first attachment section for fixing to a first bone fixation device, a second attachment section for fixing to a second bone fixation device, and said at least partially flexible intermediate section is arranged or formed between said first and second attachment sections. Said intermediate section defines at least one recess which is configured so as to enable deformation of said intermediate section. Said surgical device comprises at least one blocking element which is adapted to be brought into engagement with said intermediate section at least partially with a positively locking connection for temporarily preventing deformation of said flexible intermediate section.

In a second aspect of the invention, a spinal column stabilization system comprises at least one first bone fixation device, at least one second bone fixation device and a connecting element. Said connecting element comprises a first attachment section for fixing to a first bone fixation device, a second attachment section for fixing to a second bone fixation device, and an at least partially flexible intermediate section arranged or formed between the first and second attachment sections. Said intermediate section defines at least one recess which is configured so as to enable deformation of said intermediate section. Said spinal column stabilization system further comprises a surgical device for temporarily stiffening said flexible intermediate section of said connecting element. Said surgical device comprises at least one blocking element which is adapted to be brought into engagement with said intermediate section at least partially with a positively locking connection for temporarily preventing deformation of said flexible intermediate section.

BRIEF DESCRIPTION OF THE DRAWING FIGURES

The foregoing summary and the following description may be better understood in conjunction with the drawing figures, of which:

FIG. 2 shows a schematic perspective overall view of a surgical instrument comprising a surgical device for temporarily stiffening an at least partially flexible intermediate section, shown in FIG. 1, of a connecting element of the spinal column stabilization system;

FIG. 3 shows a perspective view of a distal end of the surgical instrument shown in FIG. 2 before gripping or after releasing the intermediate section of the connecting element;

FIG. 20 shows a side view similar to FIG. 19 of a further embodiment of a surgical device; and FIG. 21 shows a perspective view of a further embodiment of a surgical device in engagement with a flexible intermediate section of a connecting element.

DETAILED DESCRIPTION

Figure 1:
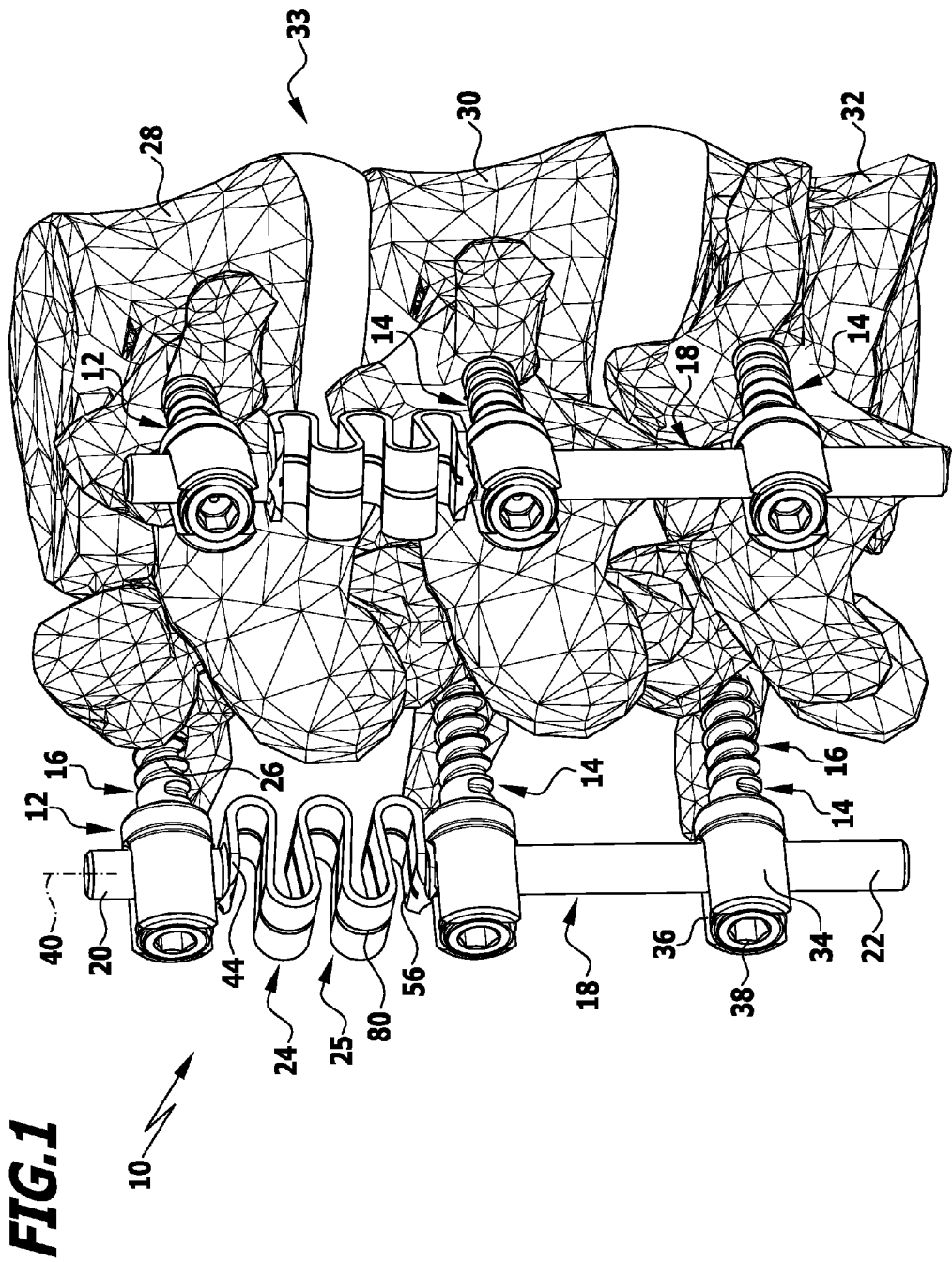
FIG. 1 shows a schematic overall view of a spinal column stabilization system fixed to a spinal column.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical device for temporarily stiffening an at least partially flexible intermediate section of a connecting element for a spinal column stabilization system, said connecting element comprising a first attachment section for fixing to a first bone fixation device, a second attachment section for fixing to a second bone fixation device, and said at least partially flexible intermediate section arranged or formed between said first and second attachment sections, said intermediate section defining at least one recess which is configured so as to enable deformation of said intermediate section, said surgical device comprising at least one blocking element which is adapted to be brought into engagement with said intermediate section at least partially with a positively locking connection for temporarily preventing deformation of said flexible intermediate section.

The solution proposed in accordance with the invention therefore provides for deformation of the intermediate section to be prevented by direct engagement therewith. For this purpose, the surgical device comprises at least one blocking element. This may be brought into engagement with the intermediate section at least partially with a positively locking connection so as to temporarily prevent undesired deformation of the flexible intermediate section, for example, when introducing and fixing the connecting element to corresponding bone fixation devices. At the same time, the at least one blocking element is able, independently of its configuration, to also protect the intermediate section so as to prevent damage thereto, in particular, undesired deformation thereof. The surgical device may, in particular, be configured in various ways. Preferred embodiments will be described hereinbelow and defined in greater detail in the subclaims. The surgical device, if configured accordingly, is able to temporarily stiffen, in particular, the connecting element in all directions of movement, i.e., prevent deformation thereof, preferably for the duration of the implantation, i.e., during introduction of the connecting element and during locking thereof to the bone fixation devices. Optionally, the surgical device may be removed after locking the bone fixation devices, i.e., after finally fixing the connecting element to these.

It is advantageous if the at least one blocking element is at least partially insertable into the at least one recess for temporarily preventing deformation of the flexible intermediate section. A blocking element inserted into a recess in the intermediate section can, in particular, block a section of the intermediate section against deformation.

Optimal effectiveness of the device can be achieved, in particular, by the at least one blocking element being configured so as to correspond or substantially correspond to a recess in the intermediate section. For example, movements in the direction of a longitudinal axis defined by the connecting element or optionally also corresponding pivotal movements about pivot axes transversely to the longitudinal axis can thus be prevented in a simple way. Furthermore, optimum temporary protection of the intermediate section may also be achieved by the corresponding configuration of the at least one blocking element.

Temporary prevention of deformation of the intermediate section is particularly easy if the at least one blocking element is insertable with a positively locking connection or substantially with a positively locking connection into a recess in the intermediate section. The at least one blocking element can thus be inserted in a simple way into the recess in the intermediate section, for example, for the duration of the implantation, and after completion of the implantation, removed from the recess again, for example, by being pulled out.

In accordance with a further preferred embodiment of the invention, the surgical device may comprise at least two retaining jaws which are movable in a direction of movement towards each other and away from each other and have retaining faces that face each other. The retaining jaws with their retaining faces can prevent in a simple way movement of the intermediate section of the connecting element in a direction transverse to the retaining faces. Depending on the configuration of the retaining jaws, one degree of freedom or even all degrees of freedom of movement of the intermediate section can thus be entirely or partly limited in each case.

It may also be advantageous if the at least two retaining jaws comprise a total of at least two axial stops that face each other and are configured so as to act relative to each other in a direction transverse to the direction of movement of the retaining jaws in order to prevent movement of the intermediate section in the axial direction. Movement of the intermediate section in the axial direction is to be understood, in particular, as deformation, i.e., compression or expansion of the intermediate section, in the axial direction. The proposed axial stops can prevent, in particular, expansion of the intermediate section and thus serve to limit a degree of freedom of movement of the intermediate section.

To ensure that the surgical device will not unintentionally release a connecting element with a blocked intermediate section, it is advantageous if the surgical device comprises a locking mechanism for preventing movement of the retaining jaws in the direction of movement away from each other in a blocking position. With the locking mechanism, the surgical device can thus be held preferably temporarily in the blocking position.

A particularly simple and compact construction of the surgical device can be achieved if at least one of the retaining jaws carries or comprises the at least one blocking element. The device may, in particular, be so configured that only one of the retaining jaws comprises one or more blocking elements. It is, however, also possible for two or more retaining jaws to each carry one or more blocking elements, which then interact to temporarily prevent movement of the intermediate section.

The at least partially flexible intermediate section can be secured against deformation in a particularly simple way if the at least one blocking element is configured in the form of a blocking projection which protrudes from a retaining face of one of the retaining jaws. Such a surgical device can also be manufactured in a simple way.

The construction and manufacture of the surgical device can be further simplified by the blocking projection being configured in the form of a cylindrical peg.

The blocking projection may advantageously be of wedge-shaped or substantially wedge-shaped configuration. This is advantageous, particularly when recesses in the intermediate section are of corresponding configuration. Degrees of freedom of movement of the intermediate section can thus be specifically blocked in more than one direction in space in a simple way.

It is particularly advantageous if the at least one blocking element is configured in the form of a blocking recess provided in the retaining face on one of the retaining jaws for at least partially receiving the intermediate section to be temporarily stiffened. In particular, it is thus also possible to receive the intermediate section entirely or partially in one or two blocking recesses in the retaining jaws. In particular, the intermediate section can in this way be particularly well protected during the implantation.

The construction of the surgical device can be further simplified when at least one of the axial stops is formed on a blocking recess. In particular, it is also possible for two axial stops which face each other to be formed on a blocking recess. The two retaining jaws with at least one, possibly also two blocking recesses, can then interact and optionally even block all of the degrees of freedom of movement of the intermediate section.

Depending on the configuration of the intermediate section, it may be advantageous if the at least two retaining jaws differ in their configuration. This means, in particular, that they may be of different shape and also carry or comprise a different number of blocking elements. In particular, it is also possible for the configurations of the blocking elements to differ from one another. For example, one retaining jaw may comprise a blocking recess, another retaining jaw a blocking projection.

It is advantageous if the retaining jaws comprise differently shaped blocking elements. This allows individual adaptation of the retaining jaws to the connecting element, i.e., in particular, to its intermediate section, in order to prevent deformation thereof, in particular, during the implantation. In particular, with differently shaped blocking elements, the surgical device as a whole can be constructed in a particularly compact manner.

In accordance with a further preferred embodiment of the invention, the surgical device may comprise a coupling device for releasably connecting the two retaining jaws to each other in a coupling position. This makes it possible, in particular, for the surgical device to be formed exclusively by two retaining jaws connectable to each other, which prior to the implantation can be brought into engagement with the connecting element and held by means of the coupling device in the coupling position. After fixing the connecting element to corresponding bone fixation devices, the surgical device can then be removed again, more specifically, by releasing the coupling device and removing the retaining jaws from the intermediate section. The latter can then become deformed in the desired manner under the effect of force in the patient's body.

The construction of the coupling device is particularly simple when it comprises first and second coupling elements which are arranged or formed, on the one hand, on the one retaining jaw and, on the other hand, on the other retaining jaw and are in engagement in the coupling position. The coupling elements may, for example, be configured in the form of latching elements. Elements screwable to each other, which may carry internal and external threads corresponding to each other, are also conceivable.

Two retaining jaws can be connected to each other and held in a coupling position particularly easily when the coupling device comprises a coupling bridge or a thread. In particular, the retaining jaws may also be held together by means of a thread. A coupling bridge protruding on a retaining jaw may, for example, penetrate a corresponding recess on the other retaining jaw and enter into a latching connection with it in the coupling position.

The preferred embodiments of surgical devices described above for temporarily stiffening an at least partially flexible intermediate section of a connecting element may, in particular, be configured such that they directly engage the intermediate section, are of small and compact configuration, and after implantation of the connecting element, can be removed from it again. To improve handling of the surgical device, it may advantageously comprise an actuating device for transferring the device from an applying position in which the device and the intermediate section are disengaged to a blocking position in which the intermediate section is held by the device in an undeformable manner on the device. The actuating device makes it possible, for example, in a simple way, to apply the device to the intermediate section and, where required, to remove it from it. The actuating device thus makes particularly simple handling of the surgical device possible.

The handling of the surgical device may, in particular, be further improved by the actuating device comprising two actuating members movable relative to each other, which are directly or indirectly coupled to the at least two retaining jaws for moving these. In other words, the retaining jaws may also be directly connected to the actuating device, so that, in particular, a surgical instrument is formed, which comprises the surgical device for temporarily stiffening an at least partially flexible intermediate section of a connecting element for a spinal column stabilization system. Such a construction allows a surgeon to use the surgical device not only for blocking the intermediate section but also for holding and inserting the connecting element as a whole during the implantation thereof. Such a surgical instrument may thus perform two functions simultaneously. Firstly, it can temporarily stiffen the intermediate section and, secondly, it can be used as holding instrument for the connecting element. This is advantageous especially in minimally invasive surgical procedures, as only limited spatial access to the operation site is possible in these cases. The instrument may, of course, also be used for percutaneous insertion of the surgical device through the muscles.

The construction of the surgical device is particularly simple when the actuating members are pivotally mounted on each other. In this way, the surgical device can, for example, be configured in the form of clamping or grasping forceps, with the retaining jaws forming distal ends of the forceps in the form of tool elements with which the intermediate section can be grasped and held.

The surgical device preferably forms part of a surgical clamping or holding instrument. As described above, the retaining jaws of the surgical device may, for example, form tool elements of surgical grasping or clamping forceps. The clamping or holding instrument may, in particular, also be configured as endoscopic tubular shaft instrument with an elongate tubular shaft, in particular, to enable use in minimally invasive surgical procedures.

In accordance with a further preferred embodiment of the invention, the surgical device may be of integral configuration and surround the flexible intermediate section with a positively locking connection. It is also possible for it to surround the flexible intermediate section only partially with a positively locking connection, but such that deformation of the intermediate section is not possible without removal of the surgical device, i.e., such that preferably all degrees of freedom of movement of the intermediate section are blocked. Integral configuration means, in particular, also that the surgical device encloses the intermediate section at least at one position in the shape of a ring or can enclose it at least partially in the shape of a ring in order to fix it in an undeformable manner in an implantation position. In this case, the surgical device can already be fixed to the intermediate section after manufacture of the connecting element and is thus already available to a surgeon as part of the connecting element. Following successful implantation of the connecting element, the surgical device can then be removed from the intermediate section again.

The surgical device can be manufactured particularly simply and cost-effectively when it is made at least partially of a material which is soluble in liquid. This makes it possible, after manufacture of the connecting element, to embed the intermediate section entirely or partially in the liquid-soluble material, which in the absence of a liquid, for example, water, has sufficient firmness to prevent deformation of the flexible intermediate section.

The surgical device can be manufactured in a particularly cost-effective and biocompatible manner when the material which is soluble in liquid is sugar or salt or when it contains sugar or salt. The surgical device can then be released from the connecting element in a simple way by flushing it with water, for example, in order to release the intermediate section.

In accordance with a further preferred embodiment of the invention, it may be provided that the surgical device is made at least partially of a material whose aggregate state is changeable for removal of the device. The material is preferably convertible from a solid to a liquid or gaseous state, for example, by changing environmental conditions such as, for example, temperature or pressure. For example, the material may be water in the form of ice or a plastic material.

It is advantageous if the surgical device is made at least partially of a material whose firmness changes permanently as a result of a change in temperature. For example, the connecting element may be provided with the surgical device and implanted at a low temperature. If the temperature is raised at least in the area of the surgical device, it can lose its firmness partially or entirely so as to permanently enable deformation of the intermediate section.

The surgical device is particularly easy to manufacture when the material is ice or a biocompatible plastic material. For example, the intermediate section can be entirely or partially enveloped in a mantle of ice in order to stiffen the intermediate section. Biocompatible plastic materials which soften when heated above their flow temperature, then lose their original stiffness and thus enable deformation of the intermediate section in the desired manner are also possible.

It is particularly advantageous if the plastic material is resorbable. This makes it possible, in particular, to first use a stiff, i.e., inflexible connecting element, whose intermediate section is stiffened by means of the surgical device. After implantation, the surgical device can be easily removed independently from the patient's body by resorption of the plastic material.

The present invention further relates to a spinal column stabilization system comprising at least one first bone fixation device, at least one second bone fixation device and a connecting element, said connecting element comprising a first attachment section for fixing to a first bone fixation device, a second attachment section for fixing to a second bone fixation device, and an at least partially flexible intermediate section arranged or formed between the first and second attachment sections, said intermediate section defining at least one recess which is configured so as to enable deformation of said intermediate section, said spinal column stabilization system further comprising a surgical device for temporarily stiffening said flexible intermediate section of said connecting element, said surgical device comprising at least one blocking element which is adapted to be brought into engagement with said intermediate section at least partially with a positively locking connection for temporarily preventing deformation of said flexible intermediate section.

Owing to the special configuration of the connecting element, such a spinal column stabilization system can be implanted particularly easily and in dependence upon the specific configuration of the surgical device for temporarily stiffening the flexible intermediate section of the connecting element and also in a way which is particularly gentle on the patient. It also has the advantages, as described at the outset, of the proposed, improved surgical device.

It is advantageous if the spinal column stabilization system comprises a surgical device for temporarily stiffening the flexible intermediate section of the connecting element, as explained in greater detail hereinabove in the form of preferred embodiments. The advantages also described there are then also accorded to the spinal column stabilization system as a whole.

It is advantageous if the intermediate section is configured in the form of a strip-shaped, wound leaf spring element and comprises at least one recess which is open at the side in a direction transverse to a longitudinal axis defined by the intermediate section. Such a leaf spring-shaped intermediate section of the connecting element is easy to manufacture, for example, from a strip-shaped material by bending or from a solid material by machining with chip removal, for example, by milling. Furthermore, the recesses may advantageously serve to receive blocking elements of the surgical device for temporarily stiffening the intermediate section.

It is advantageous if the connecting element is made of a metallic material or a plastic material. Depending on the stiffness required, one or the other material may be chosen for manufacture of the connecting element. In particular, practically any stiffnesses can be set by choice of the material. These preferably range from about 30 N/mm to 150 N/mm.

The metallic material is preferably titanium, a titanium alloy or a cobalt-chromium alloy or contains the aforementioned materials. In particular, it is a matter of biocompatible metallic materials.

The plastic material is advantageously polyetheretherketone (PEEK) or carbon fiber-reinforced polyetheretherketone (PEEK) or contains the aforementioned materials. In particular, the aforementioned materials are characterized by a high biocompatibility.

The connecting element of the spinal column stabilization system is particularly easy to manufacture when it is formed mirror-symmetrically or substantially mirror-symmetrically in relation to a mirror plane. Substantially mirror-symmetrically means, in particular, that owing to manufacturing tolerances during manufacture of the intermediate section from a solid material, a continuous leaf spring element surface is not produced, but that this may have at least one single-step shoulder owing to milling cutters introduced at a slight offset.

The stability and the bending characteristics of the connecting element can be set particularly easily and with high precision when the mirror plane contains a longitudinal axis defined by the connecting element.

In particular, excellent use can be made of the connecting element as substitute for a straight, rod-shaped connecting element when the longitudinal axis defines longitudinal axes of the attachment sections.

DETAILED DESCRIPTION

A spinal column stabilization system, generally designated by reference numeral 10, is shown schematically in FIG. 1. It comprises first bone fixation devices 12 and second bone fixation devices 14, which in the embodiment shown schematically in FIG. 1 are all configured in the form of identical bone screws 16, but may also be of different configuration. The spinal column stabilization system 10 further comprises substantially rod-shaped connecting elements 18, which comprise a first attachment section 20 for attachment to a bone screw 16, a second attachment section 22 for attachment to two bone screws 16, and an at least partially flexible intermediate section 24 in the form of a leaf spring element 25 arranged or formed between the first and second attachment sections 20, 22.

The bone screws 16 each comprise a bone anchoring section 26 with a bone thread for anchoring in a bone, for example, in one of the vertebrae 28, 30 and 32, shown schematically in FIG. 1, of a spinal column 33. Furthermore, each bone screw 16 comprises a retaining section 34 in the form of a fork head which, in an adjustment position, is mounted in an articulated manner on the bone anchoring section 26. The fork head comprises an attachment section receptacle 36 for one of the attachment sections 20, 22 of a connecting element 18. An attachment section 20, 22 introduced into the attachment section receptacle 36 can be fixed in a clamped manner in an implantation position by a clamping screw 38. By fixing the attachment section 20, 22 to the retaining section 34, a relative position between the bone anchoring section 26 and the retaining section 34 is preferably also fixed in a permanent manner.

The attachment sections 20, 22 are each of round bar-shaped configuration and, therefore, have a circular cross section. They are formed in one piece with the intermediate section 24. Preferably, as in the embodiment of a connecting element 18 shown in the Figures, the attachment sections 20 and 22 define a common longitudinal axis 40, which also defines a longitudinal axis of the intermediate section 24.

The intermediate section 24 is formed at a first end of the attachment section 20 and forms in the area of transition 42 to the attachment section 20 a substantially flat, cuboidal end plate 44. Adjoining a longitudinal side thereof transversely away from the longitudinal axis 40 is a curved section 46. This extends over an angular range of somewhat more than 180°. Adjoining the curved section 46 is a flat plane section 48, which, in turn, continues into a curved section 50 which, also facing away from the longitudinal axis 40, is convexly curved. The curved sections 46 and 50 do, however, face in opposite directions. An end face 52 of the end plate 44 facing in the direction of the second attachment section 22 is somewhat inclined to the plane section 48. Adjoining the curved section 50 is, in turn, a plane section 54 which also extends somewhat at an incline to the end face 52. The serpentine contour of the intermediate section 24 continues with a further curved section 46, a further adjoining plane section 48, an adjoining curved section 50, an adjoining plane section 54, and a last, adjoining curved section 46, which continues into an end plate 56 shaped in accordance with the end plate 44 and having an end face 58 which faces in the direction of the first attachment section 20 and also extends somewhat at an incline relative to the plane sections 54, but parallel to the end face 52.

Depending on the choice of material from which the connecting element 18 is made, a stiffness of the intermediate section 24 ranges from approximately 30 N/mm to approximately 150 N/mm. The intermediate section 24 is formed from an overall substantially flat leaf spring-shaped material or from a solid material by machining with chip removal, for example, milling or eroding. Transversely away from the longitudinal axis 40, the intermediate section 24 comprises two side faces 60 and 62 which, in a normal position in which no external forces act on the intermediate section 24, extend parallel to each other and face away from each other. These also extend parallel to a plane of symmetry 64 of the connecting element 18 containing the longitudinal axis 40 and defining a mirror plane 65.

Owing to the serpentine design of the intermediate section 24, a total of five recesses 66, 68 are formed in the embodiment shown in the Figures. The three recesses 66 face in the same direction as that in which the convexly curved sections 50 are open and face, but the two recesses 68 face in the opposite direction, i.e., in the direction in which the convexly curved sections 46 face. Each of the recesses 66, 68 defines an insertion opening 70 and 72, respectively, lying opposite a curved section 46 and 50, respectively, and facing in the respective opposite direction. Each recess 66, 68 is delimited by two plane sections 48 and 54 extending towards each other in the direction of the respective insertion opening 70, 72 so that a cross section of the respective, approximately drop-shaped recess 66, 68 increases from the insertion opening 70 and 72, respectively, in the direction towards the curved sections 46, 50 further delimiting the recesses 66, 68. Each insertion opening 70, 72 therefore defines a constriction 74. The recesses 66, 68 are, therefore, each open at the side in a direction transverse to the longitudinal axis 40.

A thickness 76 of the intermediate section 24 in the area of the curved sections 46, 50 is greater than in the area of the plane sections 48, 54. The thickness 76 is from about 1.1 times to about 1.5 times the thickness 78, preferably from about 1.3 times to about 1.35 times. In the embodiment shown in the Figures, the thickness 76 is about 0.8 mm, the thickness 78 about 0.6 mm. The thickness 76 preferably ranges from about 0.7 mm to about 0.9 mm, the thickness 78 from about 0.5 mm to about 0.7 mm. In the embodiments shown in the Figures, an inner radius of the curved sections 46, 50 is about 1.6 mm, an outer radius about 2.2 mm. Both radii may differ accordingly in dependence upon the thickness 76.

To increase the endurance strength of the connecting element 18, its outside surface 80 may be at least partially machined by a blasting process.

A surgical instrument shown in FIG. 2 and generally designated by reference numeral 80 serves to introduce the connecting element 18 with the attachment sections 20 and 22 in a defined manner into the attachment section receptacles 36 and clamp it by means of the clamping screws 38. The surgical instrument comprises an actuating device 81 with two elongate arms 82 and 84, which are mounted for pivotal movement relative to each other about a pivot axis 86. Proximal ends of the arms 82 and 84 form finger rings 88 and 90. Somewhat distally of the finger rings 88 and 90, a detent device 92 is shown schematically with two engageable detent members 94 and 96, arranged, on the one hand, on the arm 82 and, on the other hand, on the arm 84. The detent device 92, also referred to as detent, prevents movement of the finger rings 88 and 90 away from each other when the detent members 94 and 96 are in engagement with each other. The arms 82 and 84 intersect in the area of the pivot axis 86. Further towards the distal side, they are somewhat curved and each continue into a plate-shaped retaining jaw carrier 98 and 100, respectively, each having a recess.

Each of the two retaining jaw carriers 98 and 100 carries a retaining jaw 102 and 104, respectively. When the two arms 82 and 84 are pivoted towards each other, the retaining jaw carriers 98 and 100, as shown schematically in FIGS. 2 to 4, lie against each other. This position can be blocked with the detent device 92. It thus forms a locking mechanism 93 for preventing movement of the retaining jaws 102 and 104 away from each other out of a blocking position.

The retaining jaws 102 and 104 define a surgical device 106 for temporarily stiffening the flexible intermediate section 24 of the connecting element 18. For this purpose, each retaining jaw 102 and 104 has a plurality of blocking elements 108 and 110, respectively, which are engageable with the intermediate section 24 at least partially with a positively locking connection for temporarily preventing deformation of the flexible intermediate section 24. The retaining jaws 102 and 104 define plane retaining faces 112 and 114 which face each other.

The retaining jaw 102 has three identical blocking elements 108 in the form of blocking recesses 116 provided on the retaining jaw 102 in the retaining face 112 for partially receiving the leaf spring element 25, more specifically, in the area of the curved sections 46. The blocking recesses 116 are arranged symmetrically alongside one another. They are formed so as to correspond to the shape of the leaf spring element 25 and each define a substantially U-shaped groove, which is open in the direction towards a front side 118 of the retaining jaw 102. Side faces 120 and 122, substantially facing each other, of the two outer blocking recesses 116 extend substantially transversely to the longitudinal axis 40 and form axial stops 124 and 126 against which the end plates 44 and 56 abut. When the leaf spring element 25 is in engagement with the blocking recesses 116 of the retaining jaw 102, then the leaf spring element 25 is stiffened substantially in the direction of the longitudinal axis 40, i.e., in the axial direction.

Figure 5:
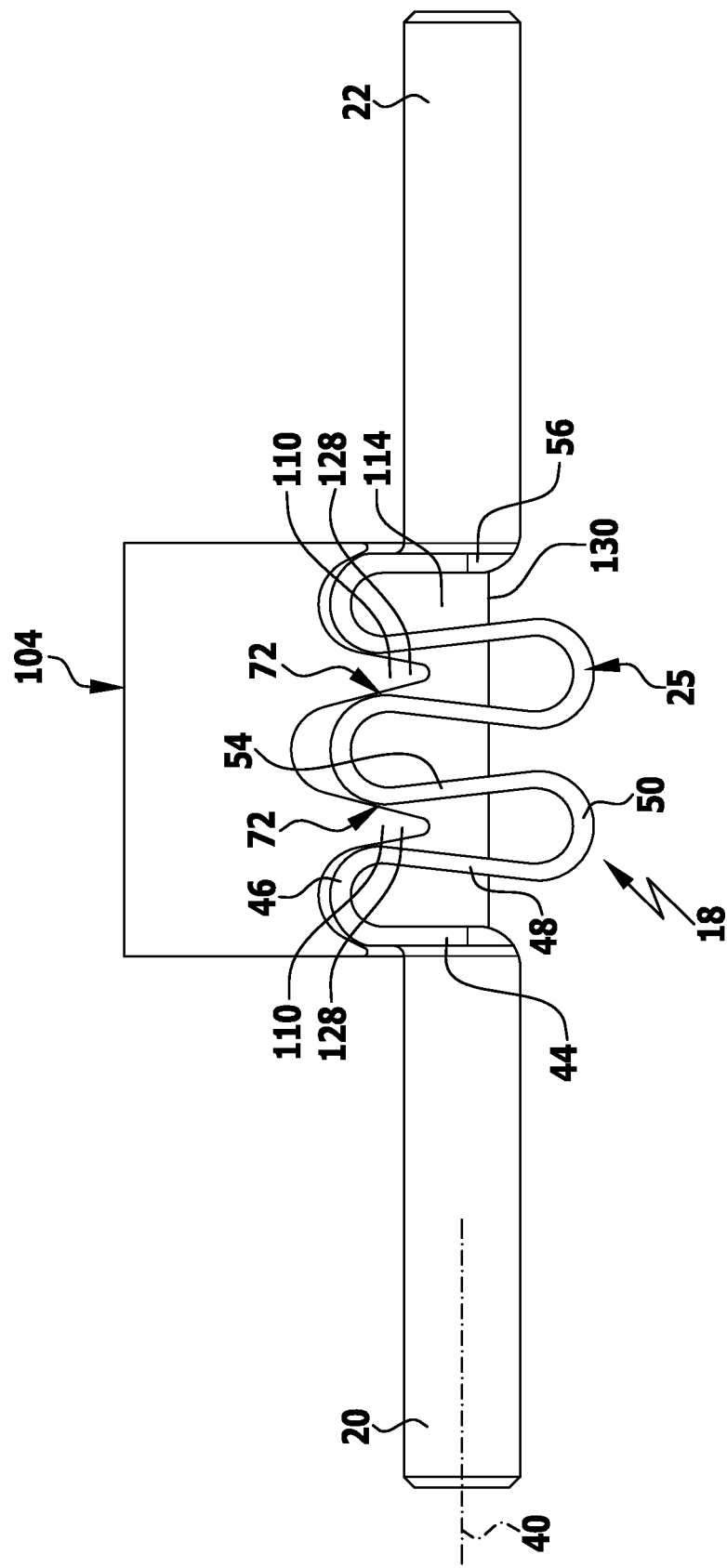
FIG. 5 shows a schematic representation of a retaining jaw of the surgical device from FIGS. 2 and 3 in engagement with the intermediate section.
Figure 6:
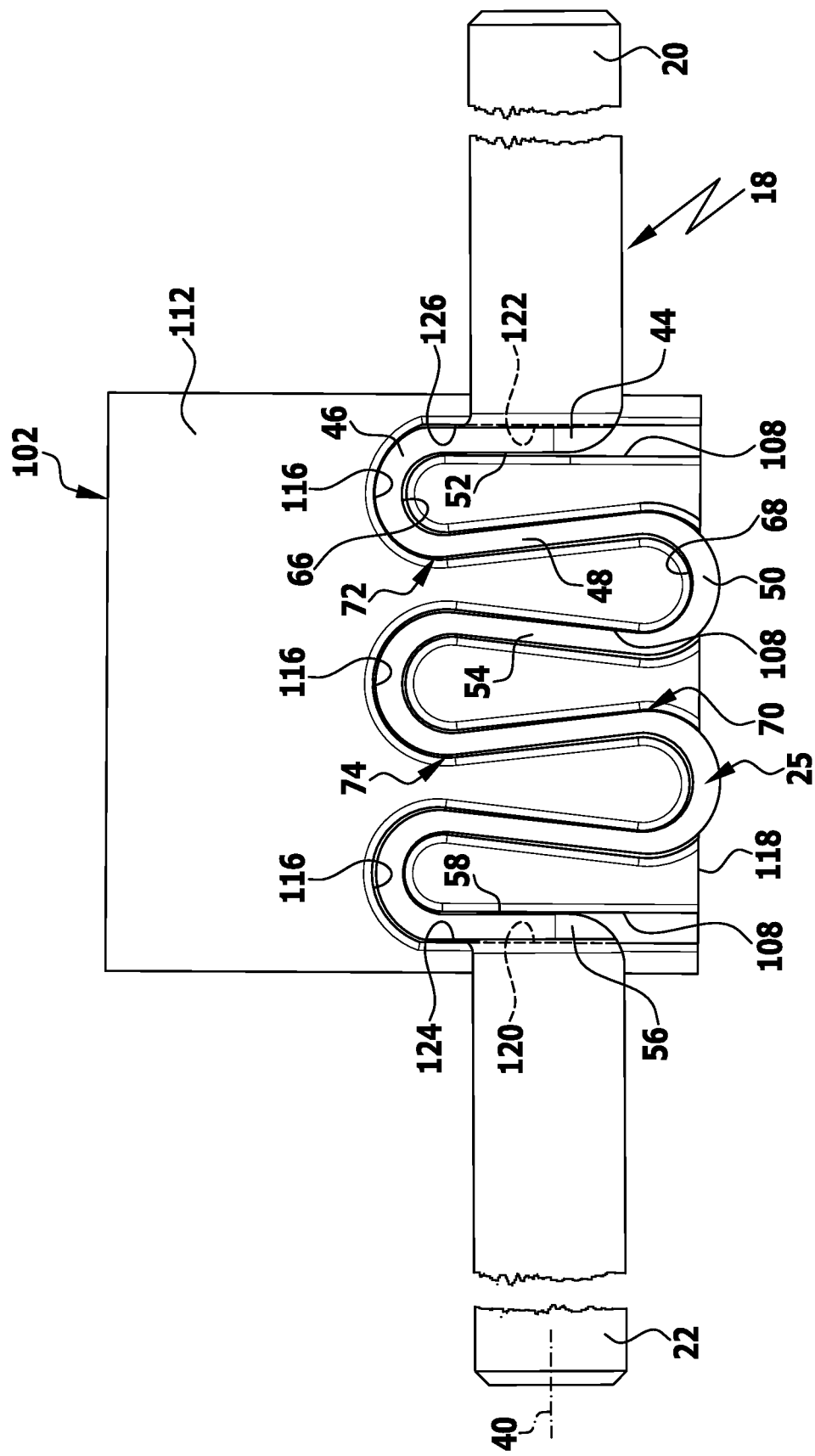
FIG. 6 shows a view in analogy with FIG. 4 of an alternative embodiment of a retaining jaw.

The retaining jaw 104 has two blocking elements 110 in the form of tooth-like blocking projections 128. These are formed in raised configuration on the retaining face 114 so as to protrude therefrom. With their tips, they point in the distal direction towards a front edge 130 of the retaining jaw 104. The blocking projections 128 are of such configuration that, as shown schematically in FIG. 5, they engage the insertion openings 72 between the curved sections 46 and thus protrude partially into the recesses 68. A deformation of the leaf spring element 25 is thereby additionally blocked. The side face 60 then lies directly against the retaining face 114, the side face 62 of the leaf spring element 25 lies with part thereof against groove bottoms, facing in the direction towards the retaining face 114, of the groove-shaped blocking recesses 116. The leaf spring element 25 is therefore held between the retaining jaws 102 and 104, which prevent movement of the leaf spring element 25 in a plane transverse to the longitudinal axis 40. Thus, all degrees of freedom of the leaf spring element 25 are blocked by the device 106. The connecting element 18 is, therefore, temporarily stiffened and deformation of the leaf spring element 25 is prevented.

With the instrument 80, a surgeon can grip or grasp the connecting element 18 in the described manner shown in FIGS. 2 to 6, temporarily stiffen the leaf spring element 25 and insert it using the instrument 80 into the attachment section receptacles 36 of the bone fixation devices 12 and 14. The connecting element 18 can be held with the instrument 80, in particular, for such a time until the attachment sections 20 and 22 are fixed in the desired manner with the clamping screws 38 to the bone fixation devices 12 and 14. Once this is the case, the surgeon can release the detent device 92 again, if activated, and pivot the two retaining jaws 102 and 104 away from each other in order to release the leaf spring element 25 again. Owing to the mounting of the arms 82 and 84 for pivotal movement about the pivot axis 86, the retaining jaws 102 and 104 are also movable in a direction of movement relative to each other. In the embodiment shown in FIGS. 2 to 5, they are pivotable towards each other.

Figure 3A:
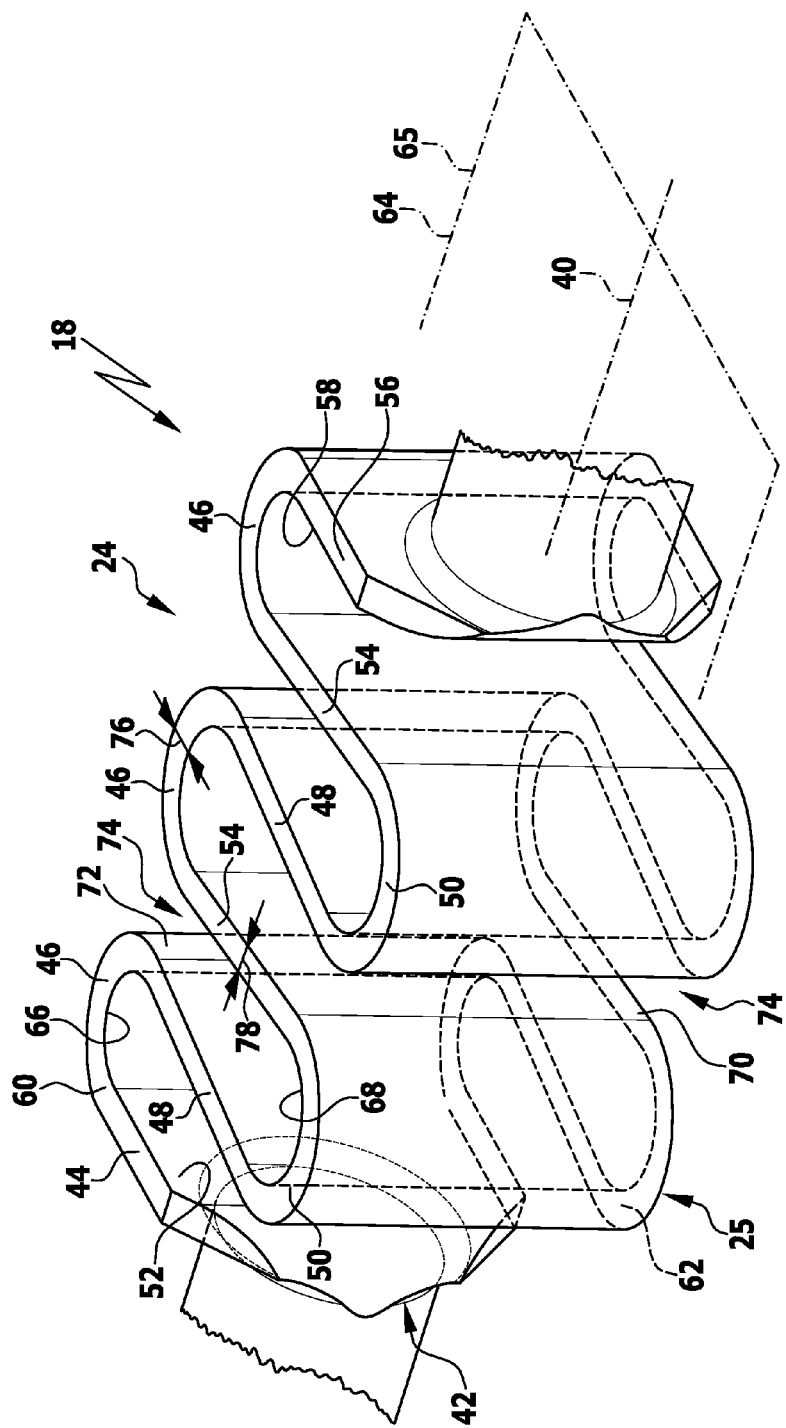
FIG. 3A shows an enlarged view of area A in FIG. 3.
Figure 4:
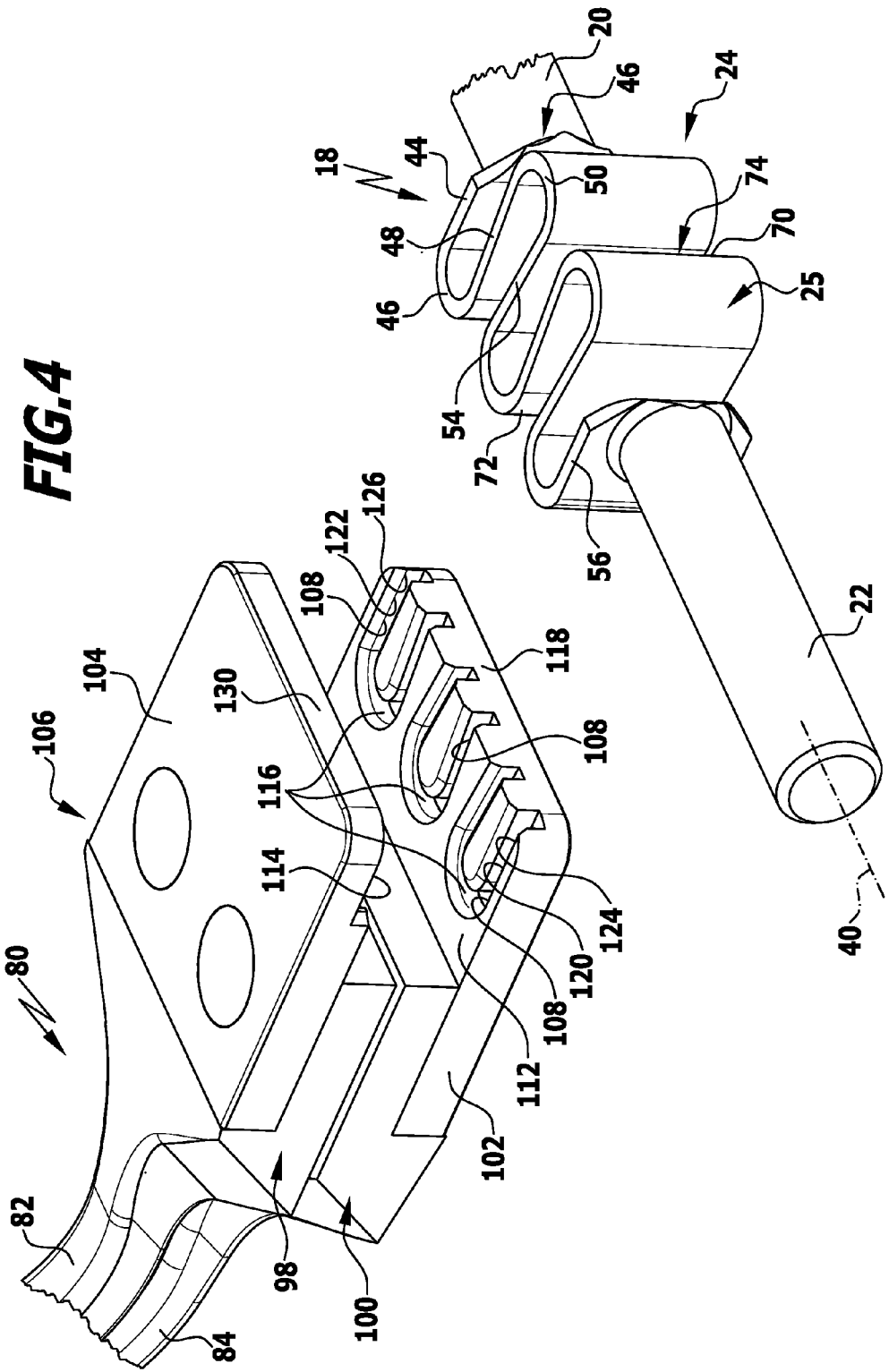
FIG. 4 shows a view similar to FIG. 3 of the surgical instrument from FIG. 3 from the opposite side.

In this way, the detent device 92 forms a locking mechanism 93 for preventing movement of the retaining jaws 102 and 104 in a direction of movement away from each other when the retaining jaws 102 and 104 assume a blocking position, as shown schematically in FIGS. 2 to 4.

The retaining jaws 102 and 104 may optionally form the device 106 without the actuating device 81. In this case, the retaining jaws 102 and 104 are attached either directly to the intermediate section 24 or to each other when they are in engagement with the leaf spring element 25, for example, with a thread, not shown, or a clip.

Figure 7:
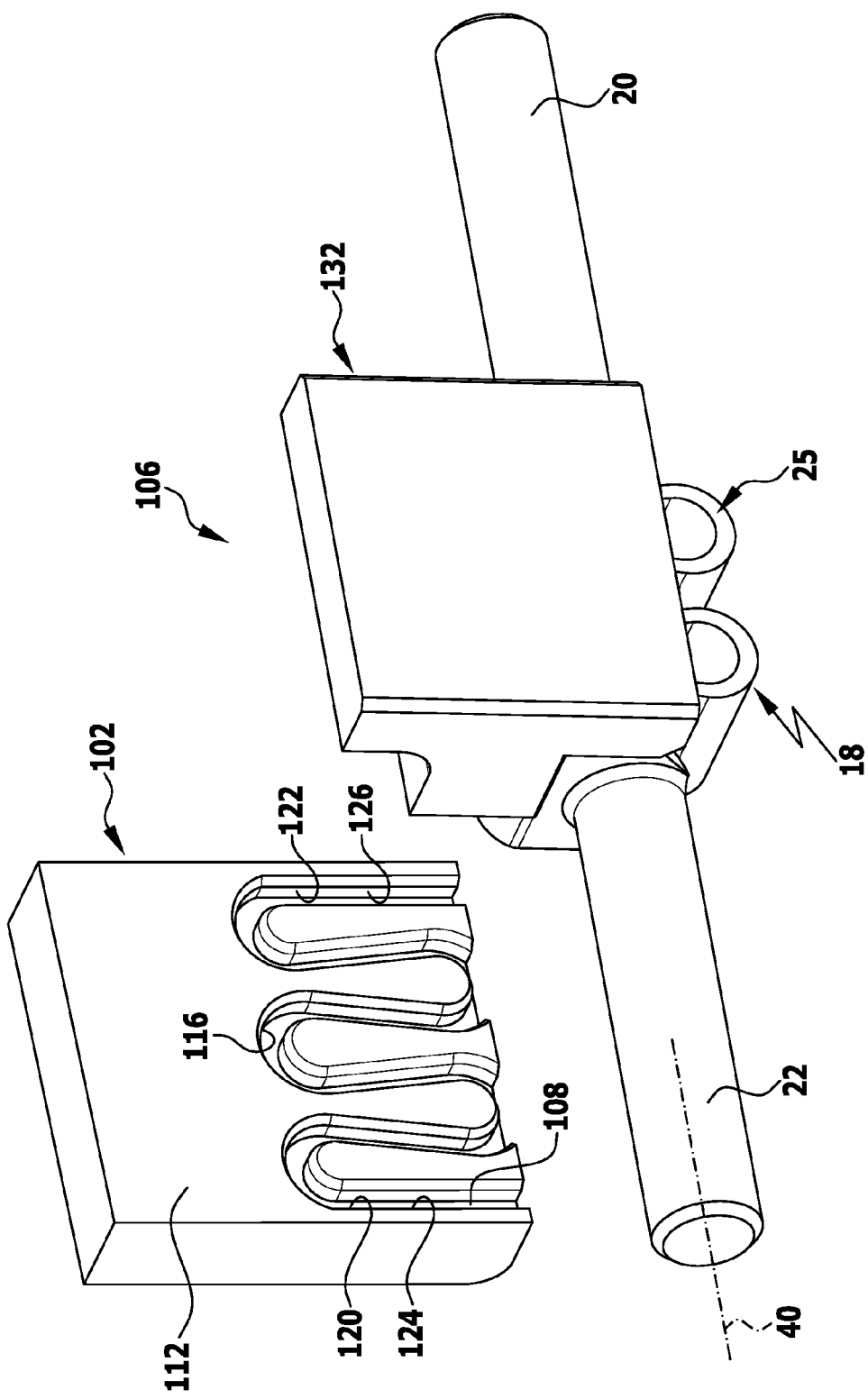
FIG. 7 shows a schematic overall view of the connecting element with the retaining jaws shown in FIGS. 5 and 6 for formation of a surgical device for stiffening the intermediate section.
Figure 8:
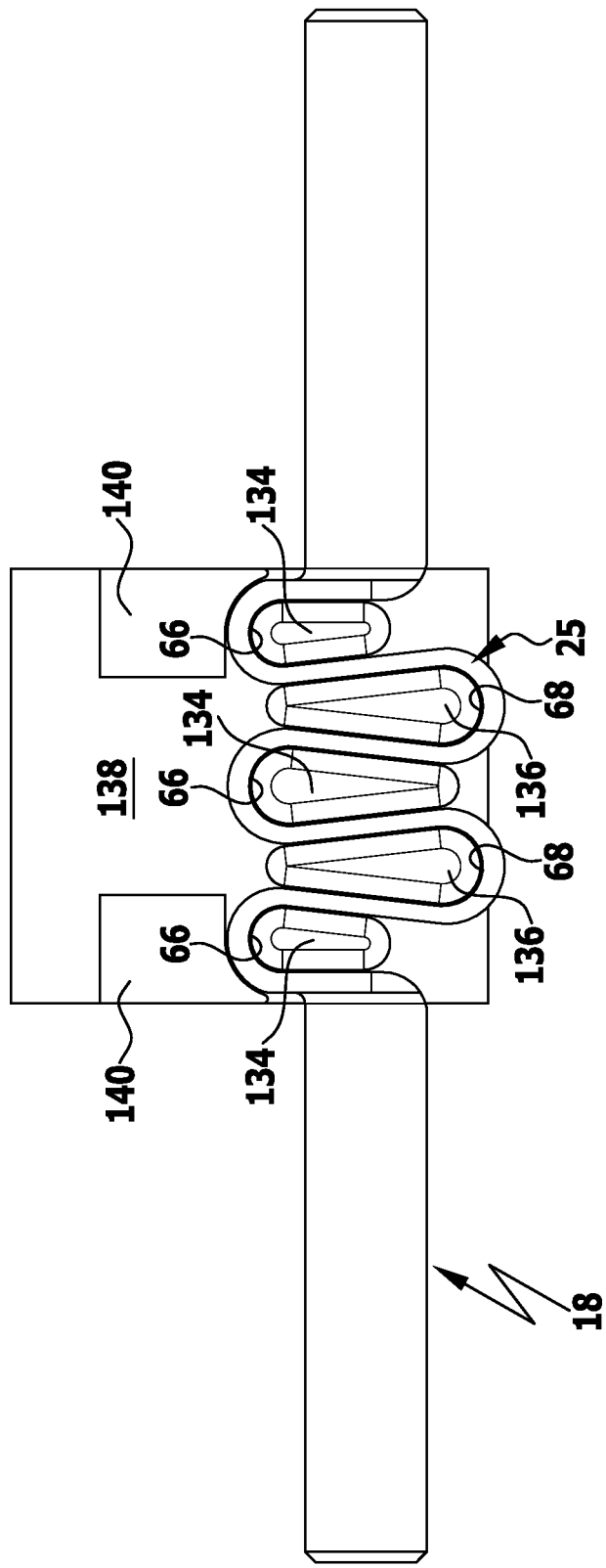
FIG. 8 shows a schematic side view of a further embodiment of a retaining jaw of the surgical device in a side view in engagement with the intermediate section of the connecting element.

A further embodiment of a surgical device 106 is shown in FIGS. 7 and 8. This comprises a retaining jaw 102 and a retaining jaw 132, which is similar in configuration to the retaining jaw 104. The retaining jaw 132 has a total of five blocking projections 134, 136, with the three blocking projections 134 being configured so as to correspond to the recesses 66, and the two blocking projections 136 so as to correspond to the recesses 68. They project from a retaining face 138, which faces towards the retaining face 112 of the retaining jaw 102. There also protrude from the retaining jaw 132, i.e., from its retaining face 138, two projections substantially facing each other and defining axial stops 140, against which a curved section 46 partially lies, in each case, more specifically, in the area of the transition to the two end plates 44 and 56. The retaining jaw 132 together with the retaining jaw 102 thus enables a complete stiffening of the intermediate section 24 when they are in engagement with the leaf spring element 25.

Figure 9:
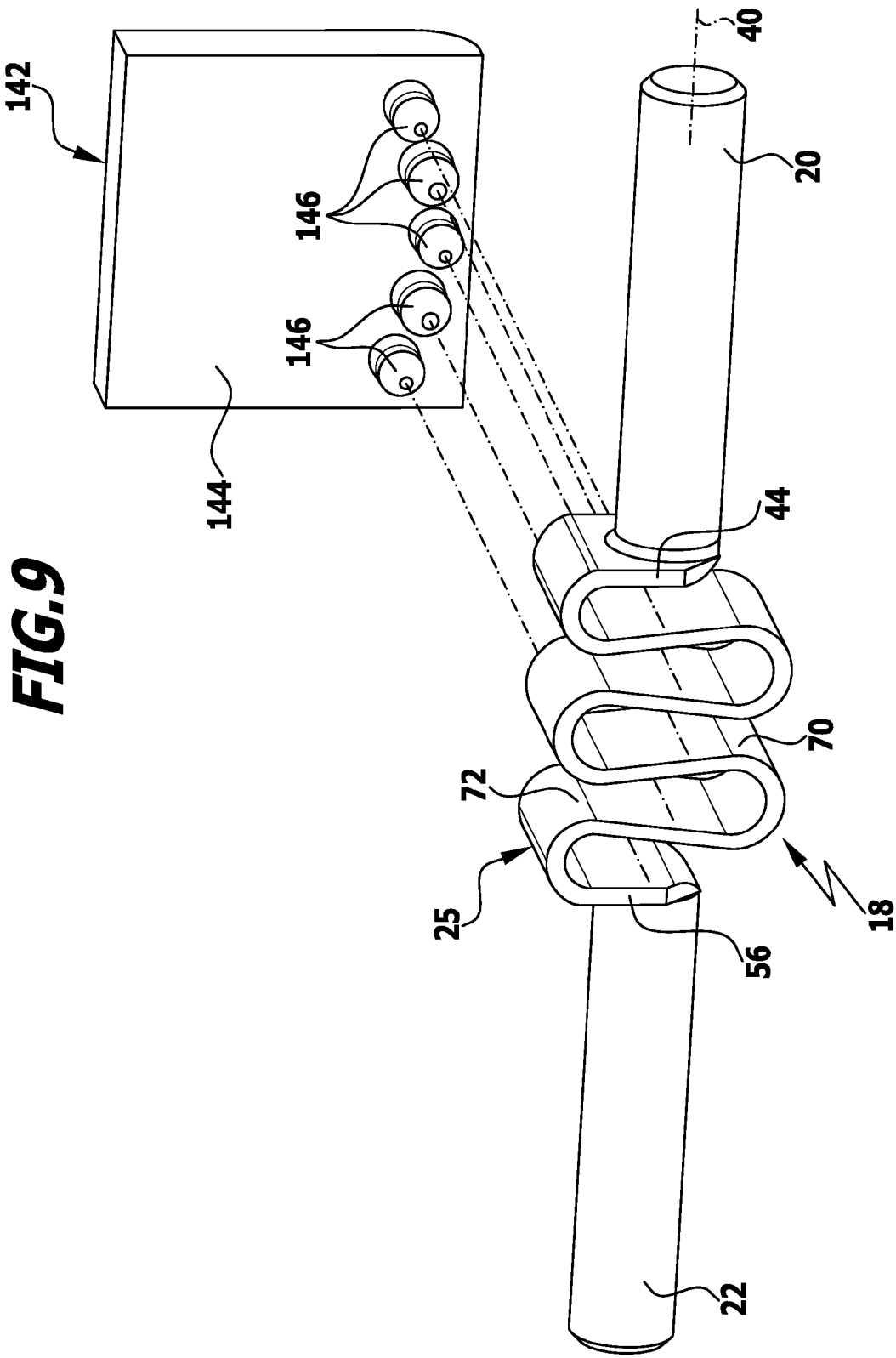
FIG. 9 shows a perspective view of a further embodiment of a retaining jaw before being brought into engagement with the intermediate section of the connecting element.
Figure 10:
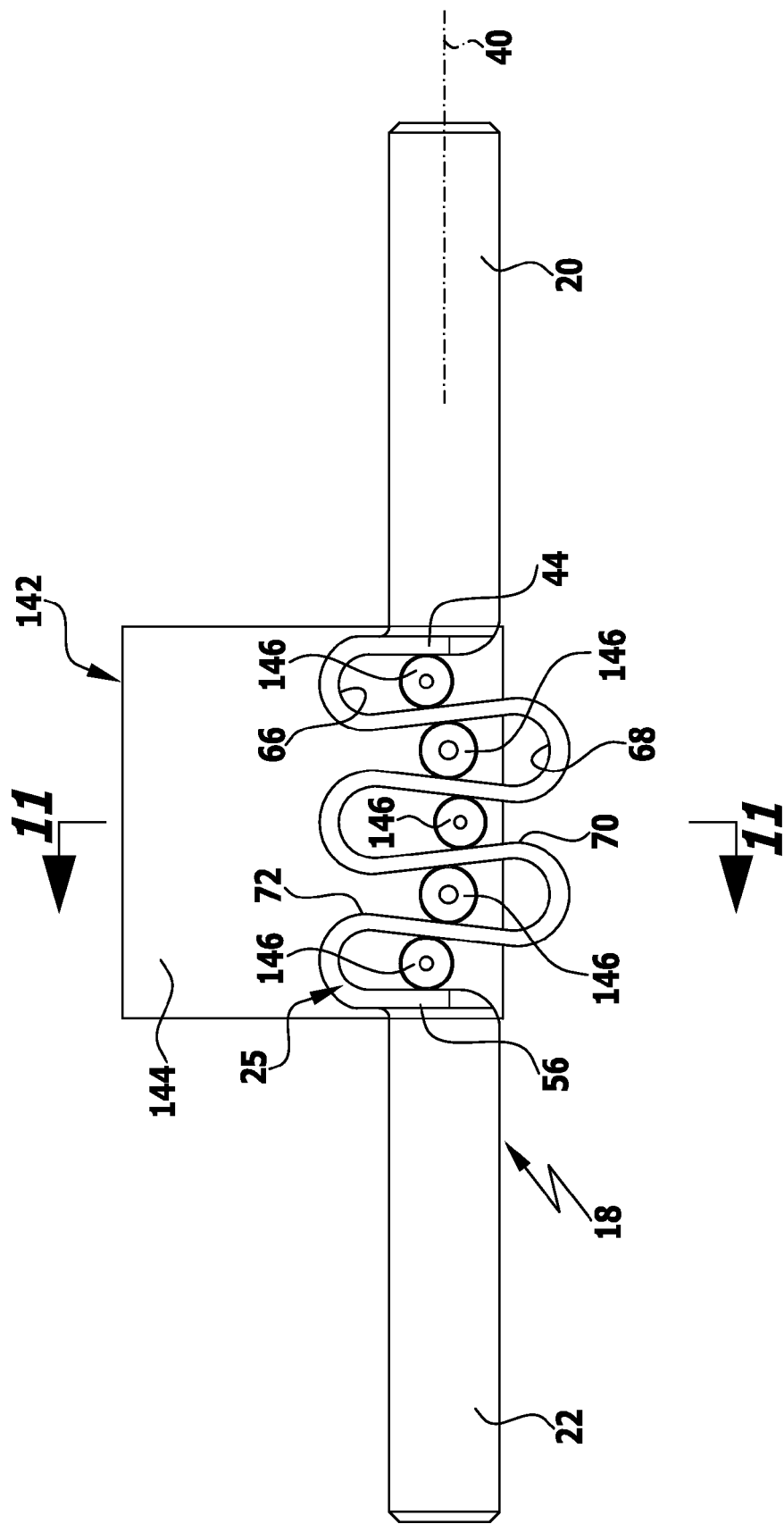
FIG. 10 shows a side view of the retaining jaw from FIG. 9 in engagement with the intermediate section.
Figure 11:
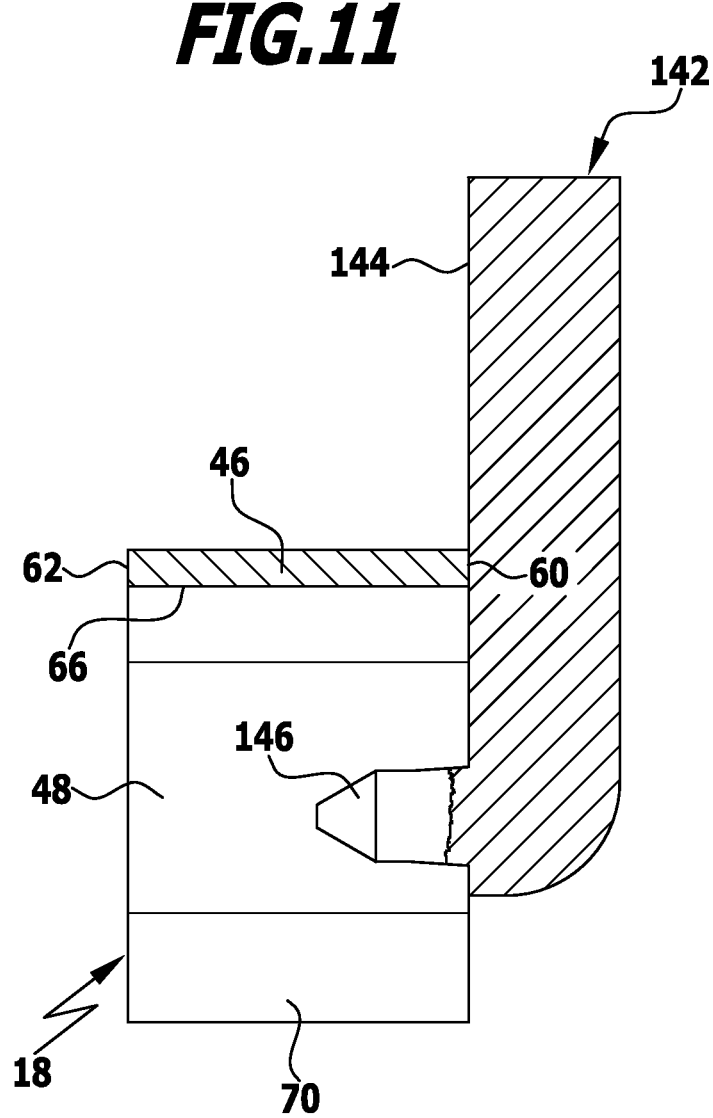
FIG. 11 shows a sectional view along line 11-11 in FIG. 10.

A retaining jaw 142, shown in FIGS. 9 to 11, may, for example, be used instead of the retaining jaw 104. It comprises a cuboidal plate, which defines a retaining face 144, and from which a total of five blocking elements 146 in the form of substantially cylindrical blocking projections protrude. These are arranged so as to engage the recesses 66 and 68, more specifically, in each case, between two straight-lined sections 48 and 54 of the leaf spring element 25 or between a straight-lined section 48 and one of the two end plates 44 and 56. Together with a further retaining jaw, which may be configured in the form of one of the retaining jaws 102, 104 or 132, a surgical device 106 for temporarily stiffening the intermediate section 24 may thus also be formed. Like all of the retaining jaws described above, the retaining jaw 142 may, of course, form part of the instrument 80.

Figure 12:
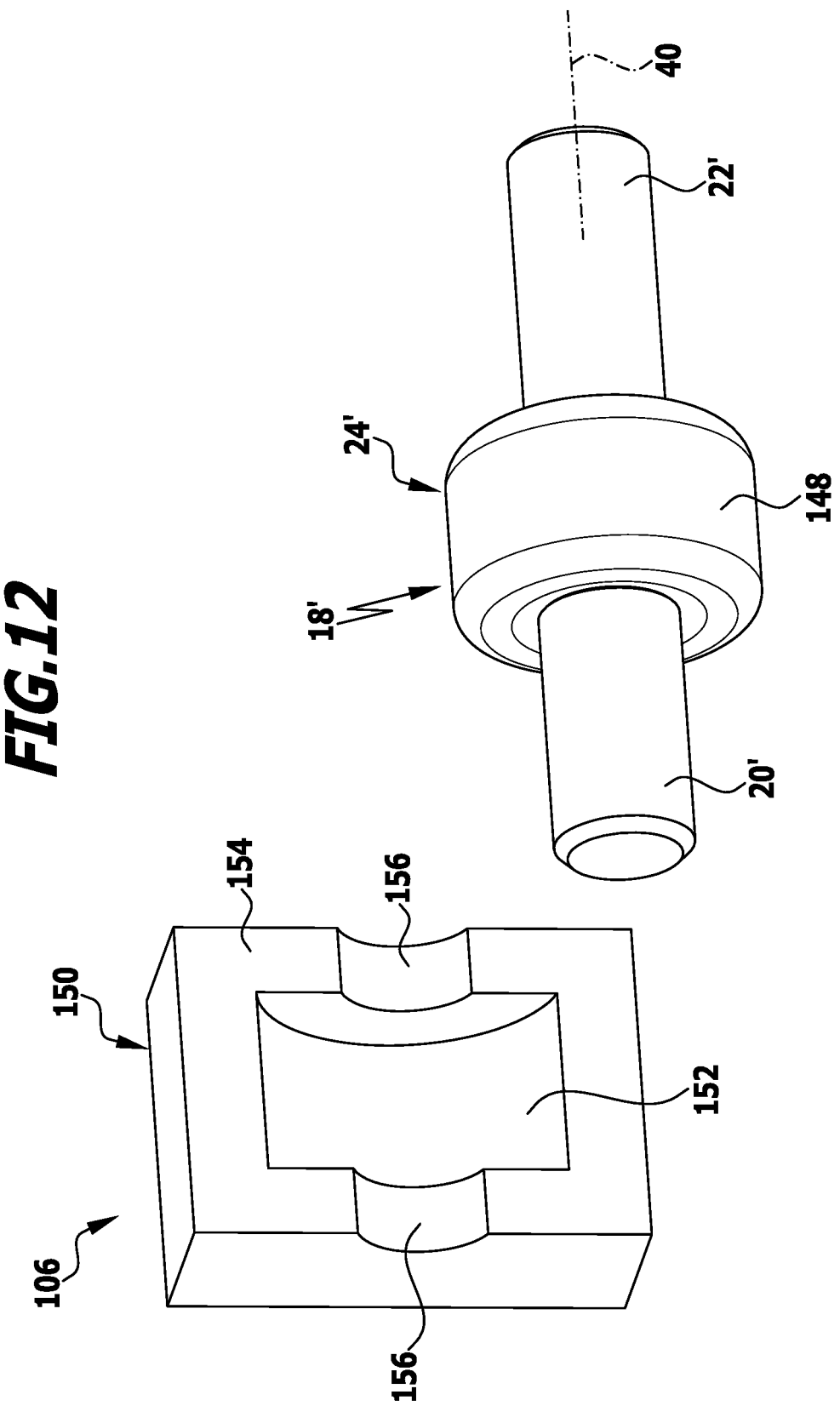
FIG. 12 shows a schematic perspective view of a further embodiment of a retaining jaw before being applied to a connecting element with a flexible intermediate section.
Figure 13:
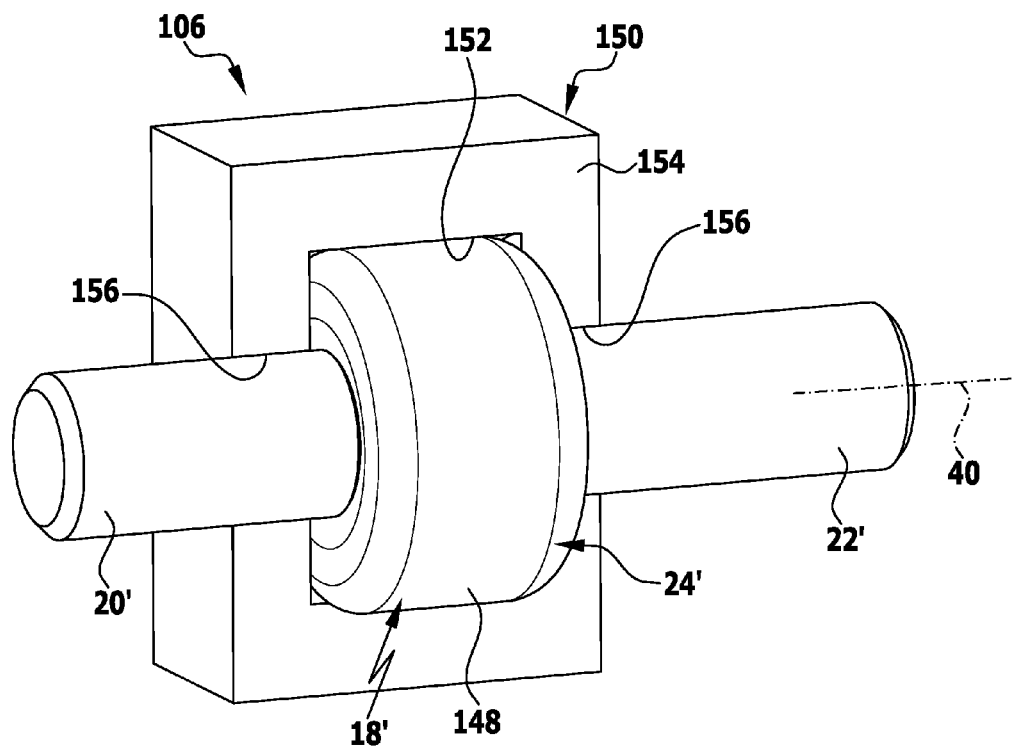
FIG. 13 shows a schematic perspective view of the retaining jaw from FIG. 12 in engagement with the flexible intermediate section.
Figure 14:
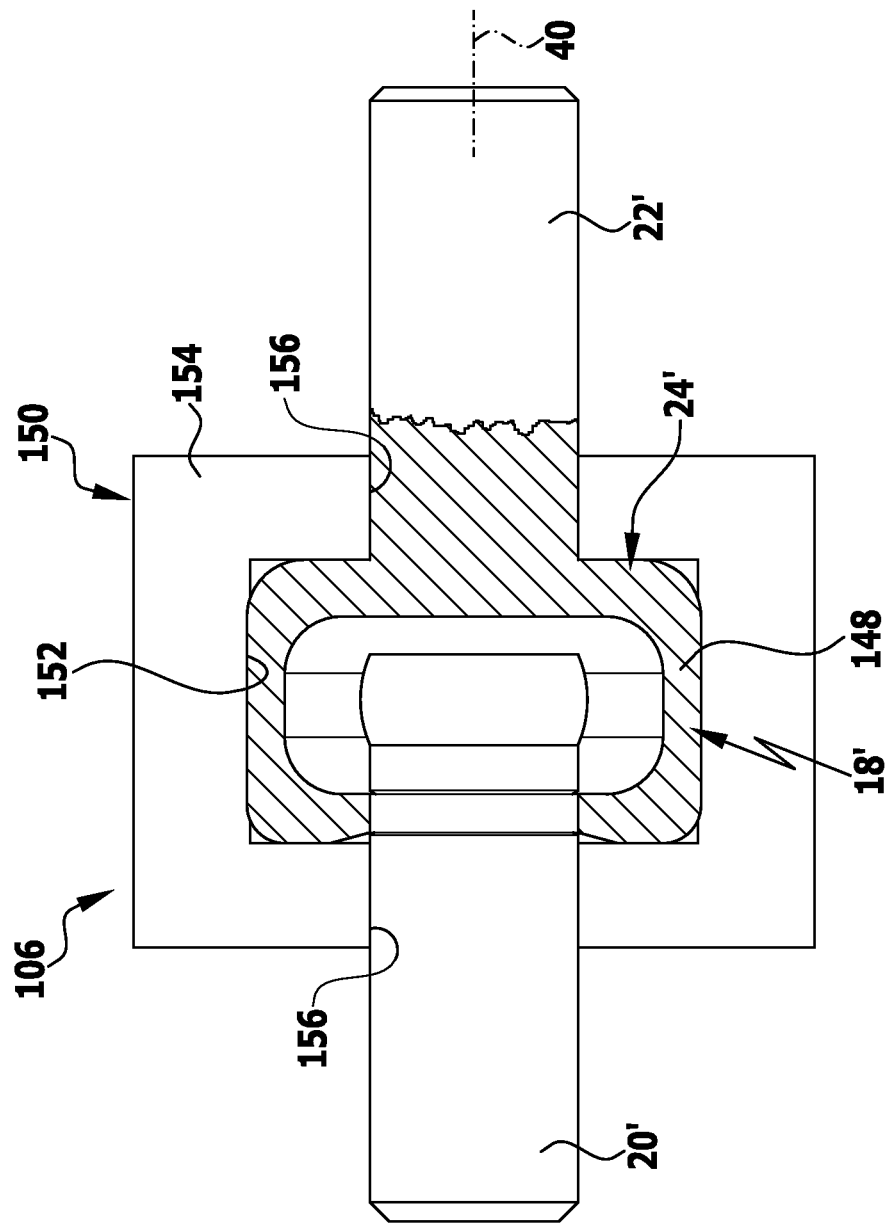
FIG. 14 shows a partially broken-open side view of the arrangement shown in FIG. 13.

A connecting element, generally designated by reference numeral 18', comprising two rod-shaped attachment sections 20' and 22' coupled to each other by a hollow-cylindrical coupling element 148, is shown in FIGS. 12 to 14. The coupling element 148 is of partially flexible or deformable configuration and enables damped movement of the attachment sections 20' and 22' relative to each other both in the direction of a longitudinal axis 40 of the connecting element 18' and transversely thereto. To prevent movement of the attachment sections 20' and 22' relative to each other, the coupling element 148 defining an intermediate section 24' can be temporarily stiffened by means of a further variant of a surgical device 106. Two retaining jaws 150 of identical configuration, which each comprise a blocking recess 152, which has the shape of a half cylinder and can, therefore, receive half of the coupling element 148 with a positively locking connection, preferably serve this purpose. The blocking recess 152 is formed in a retaining face 154 of the retaining jaw 150. Semicircular rod receptacles 156 for receiving the attachment sections 20' and 22' adjoin the blocking recess 152.

Thus, the coupling element 148 can be substantially completely enclosed by the two identical retaining jaws 150, so that deformation of the intermediate section 24' is prevented in all directions in space.

Figure 15:
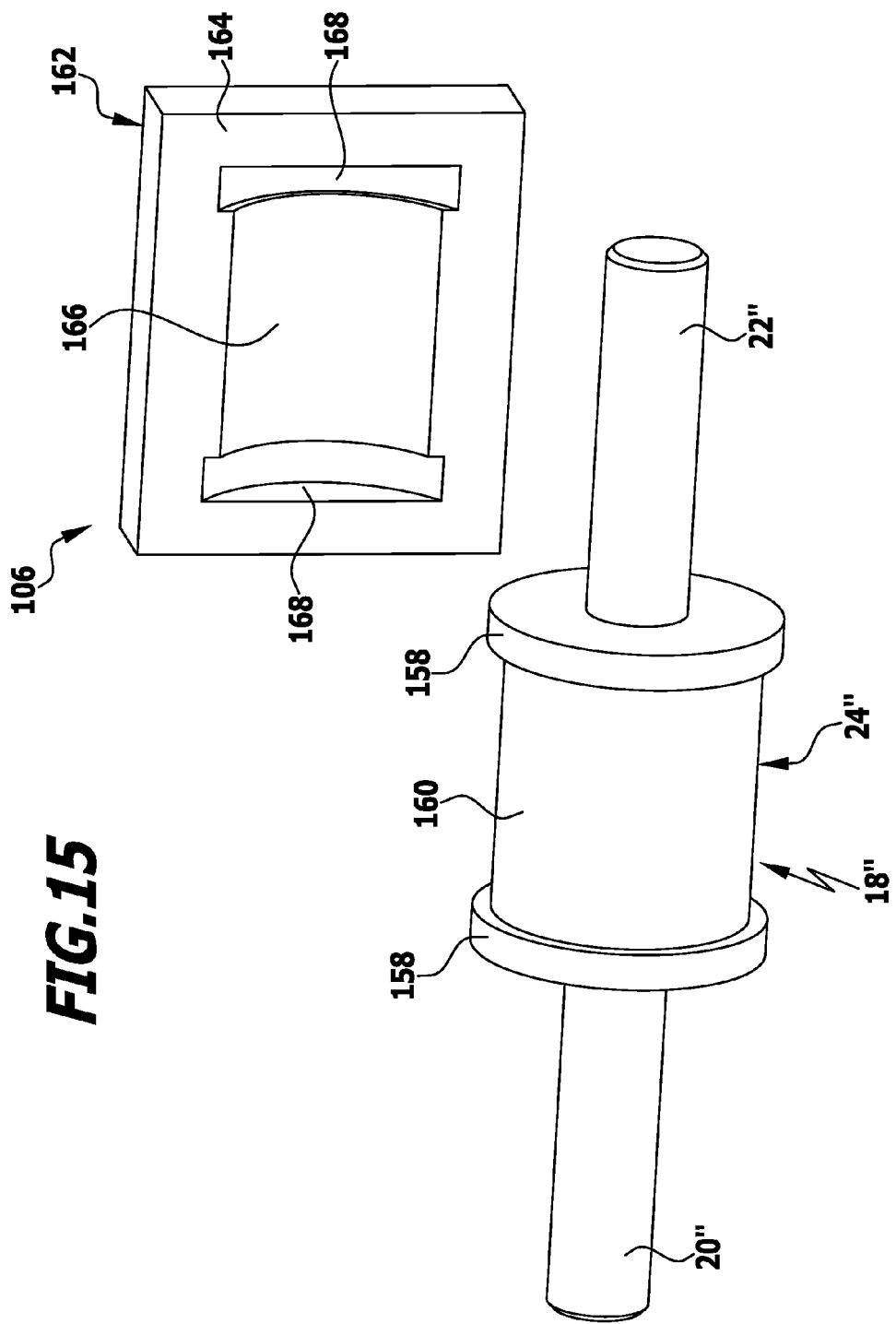
FIG. 15 shows a schematic perspective view of a further embodiment of a retaining jaw before being applied to a connecting element with a flexible intermediate section.

A further embodiment of a connecting element 18" comprising two rod-shaped attachment sections 20" and 22", which are each provided at one end with a disc-shaped carrier plate 158, is shown schematically in FIG. 15. The carrier plates 158 face each other. An elastic element 160 of cylindrical shape is arranged between the carrier plates 158. The intermediate section 24" is thus formed by the two carrier plates 158 and the elastic element 160 held between these. An outer diameter of the carrier plates 158 is somewhat larger than that of the elastic element 160.

Two identical retaining jaws 162, one of which is shown schematically in FIG. 15, are preferably provided for forming a further surgical device 106. The retaining jaw 162 is configured in the form of a cuboidal plate and defines a planar retaining face 164. Extending from the retaining face 164 into the retaining jaw 162 is a blocking recess 166, which can receive the intermediate section 24" partially with a positively locking connection. The blocking recess 166 is thus formed so as to correspond substantially to a part, for example, a half, of the intermediate section 24". The flexible intermediate section 24" can be temporarily stiffened with two retaining jaws 162. Side faces 168 of the blocking recess 166 which face each other form axial stops for the intermediate section 24". When the intermediate section 24" is held in the blocking recess 166, the carrier plates 158 lie, in each case, against the side faces 168 of the two retaining jaws 162. All degrees of freedom of movement of the connecting element 18" are blocked by the two retaining jaws 162 jointly.

Figure 16:
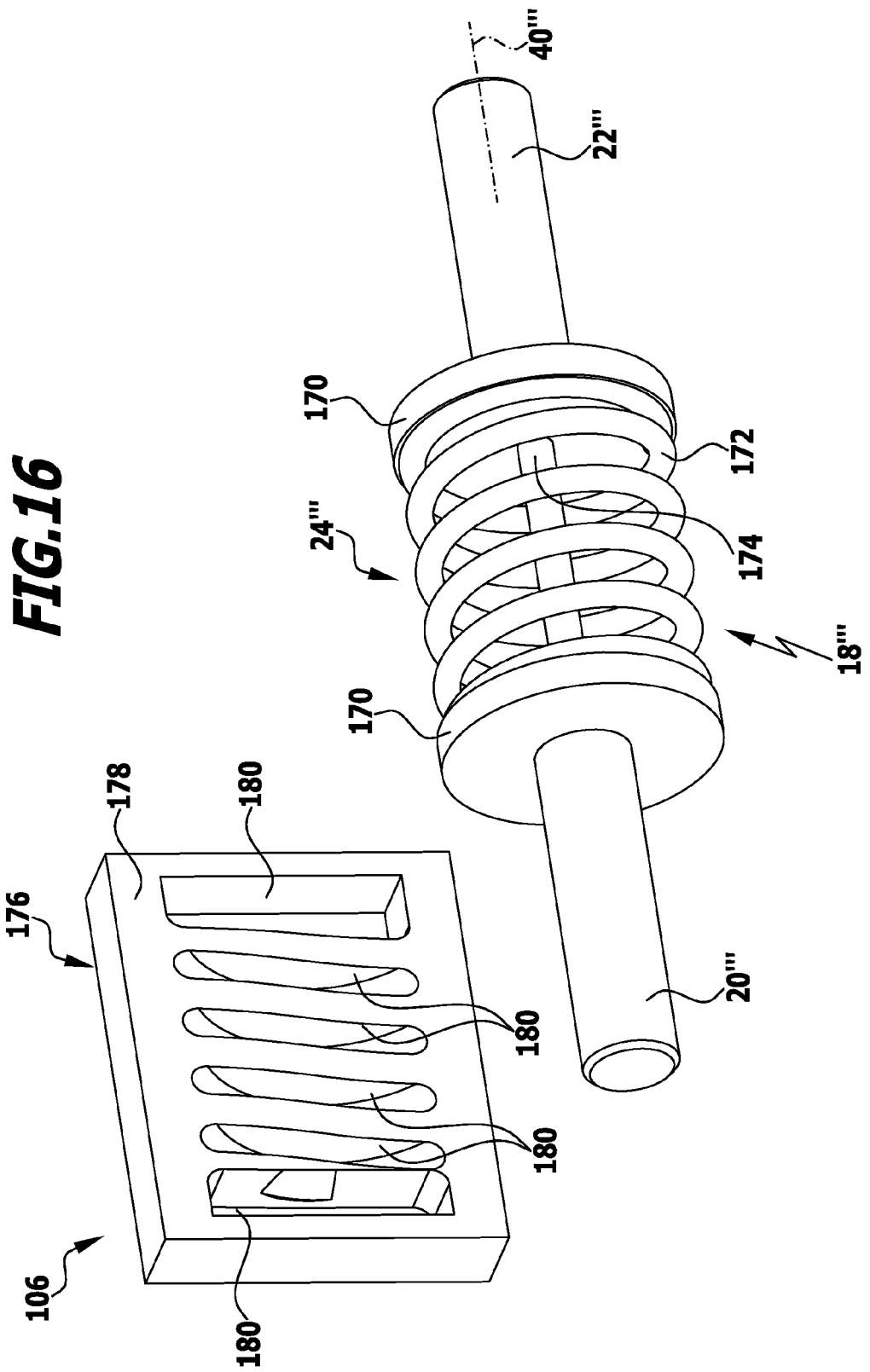
FIG. 16 shows a schematic perspective view of a further embodiment of a retaining jaw before being applied to a connecting element with a flexible intermediate section.
Figure 17:
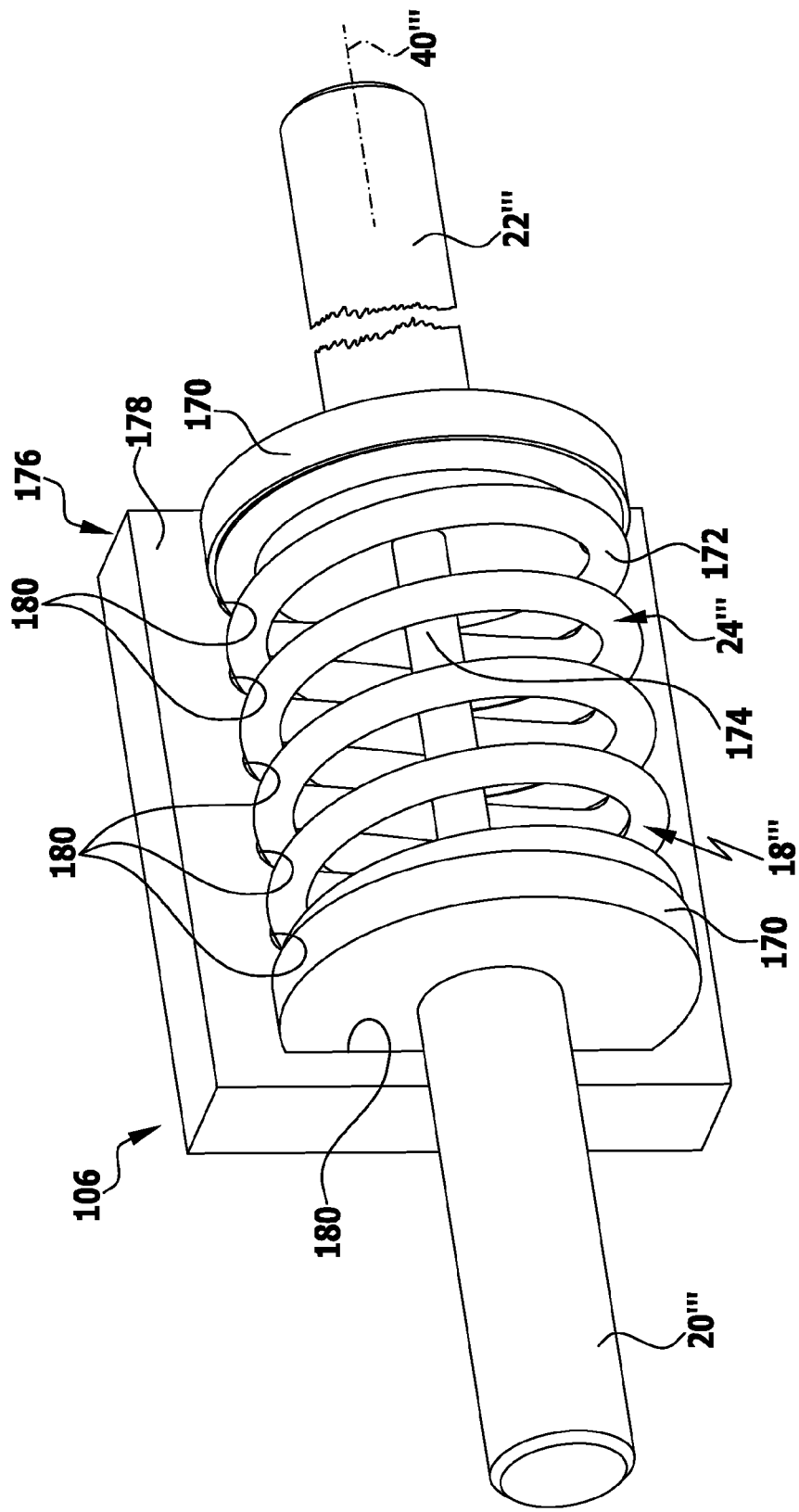
FIG. 17 shows a schematic perspective view of the retaining jaw from FIG. 16 in engagement with the flexible intermediate section.

A further embodiment of a connecting element generally designated by reference numeral 18''' is shown schematically in FIGS. 16 and 17. It comprises two rod-shaped attachment sections 20''' and 22''', which each have at a free end a disc-shaped carrier plate 170. The carrier plates 170 are arranged so as to face each other. A helical spring 172 whose outer diameter matches the outer diameter of the carrier plates 170 is arranged between the carrier plates 170. In addition, a guide rod 174 is provided, which protrudes perpendicularly from a carrier plate 170 and engages a bore in the opposite carrier plate 170, which continues in the associated attachment section 20''' or 22''' This special configuration makes it possible to move the carrier plates 170 towards each other counter to the action of the helical spring 172. Rotation of the carrier plates 170 about the longitudinal axis 40''' may be possible, but owing to the guide rod 174 being provided, movement in a direction transverse to the longitudinal axis 40''' is not possible.

A further retaining jaw 176, which together with a further retaining jaw 176 of identical configuration forms a further surgical device 106 for temporarily stiffening the intermediate section 24''' formed by the carrier plates 170 together with the helical spring 172, is shown schematically in FIGS. 16 and 17. The cuboidal retaining jaw 176 has a planar retaining face 178 in which a plurality of blocking recesses 180 are formed for partially receiving the carrier plates 170 and the helical spring 172. When, in an analogous manner, as shown in FIG. 17, a further retaining jaw 176 is made to engage the intermediate section 24''' from the side, i.e., transversely to the longitudinal axis 40''', the intermediate section 24''' can be temporarily stiffened.

The retaining jaws 150, 162 and 176 described above may also form in the manner described above part of a surgical instrument 80 in order to temporarily stiffen the respective connecting elements. They may, however, also be directly coupled to each other or connected in some other way, for example, with a thread or a coupling device in order to prevent deformation of the connecting elements during implantation.

Figure 18:
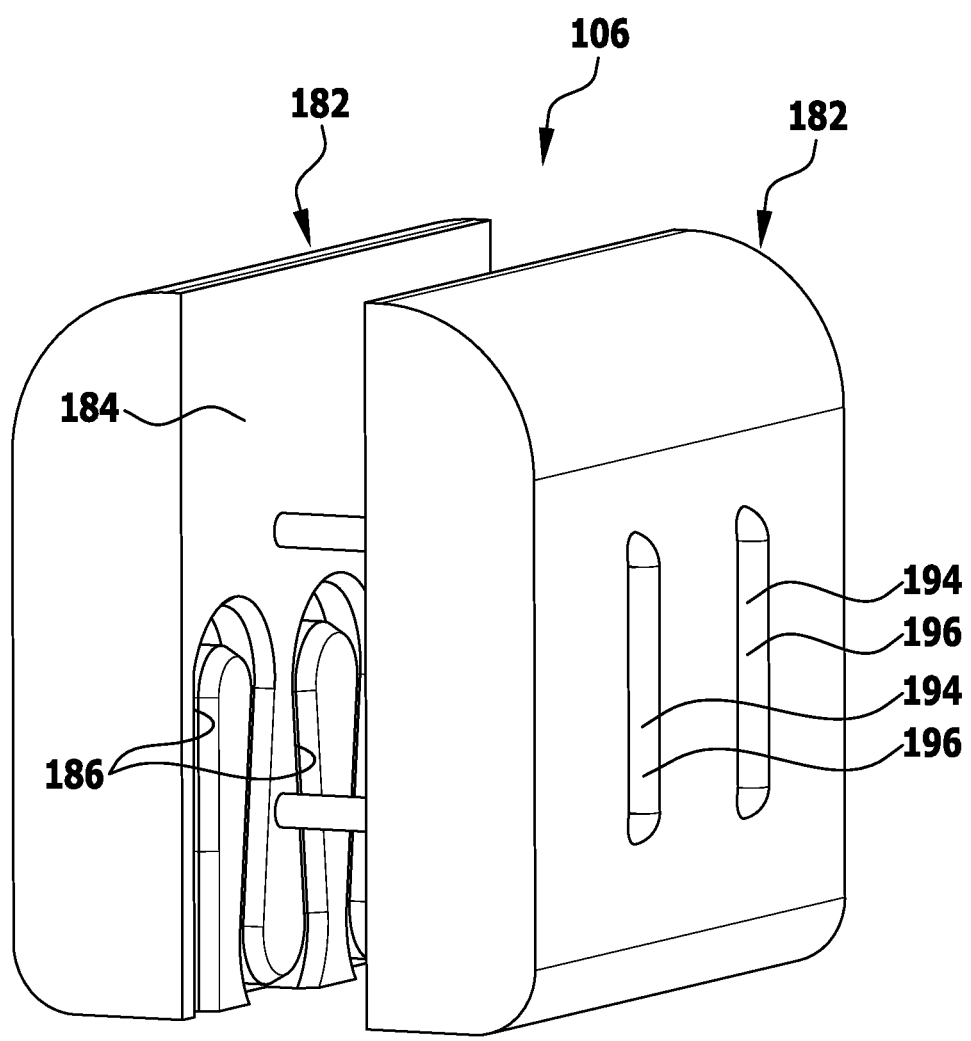
FIG. 18 shows a schematic perspective view of a surgical device comprising two retaining jaws coupled by means of a coupling device.
Figure 19:
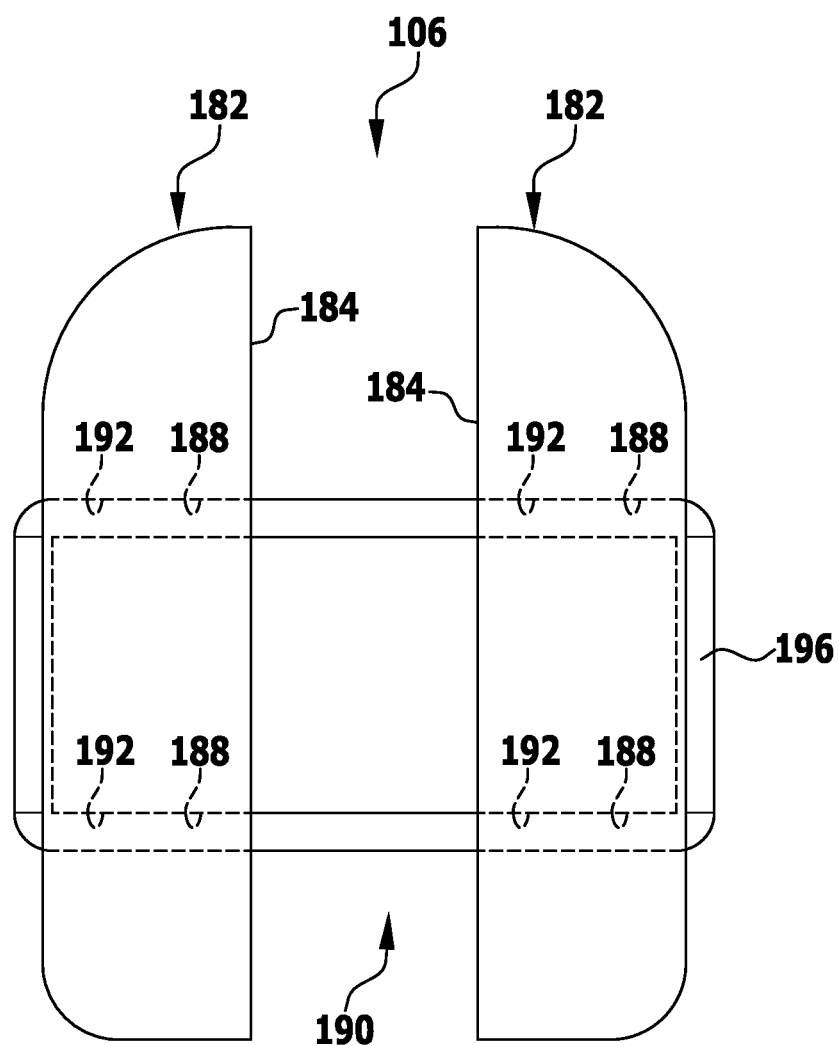
FIG. 19 shows a side view of the surgical device shown in FIG. 18.

A further variant of a surgical device 106 comprising two identical retaining jaws 182 is shown in FIGS. 18 and 19. A plurality of blocking recesses 186, corresponding to the blocking recesses 116, are formed in retaining faces 184 of the retaining jaws 182 that face each other. This makes it possible to temporarily fix, for example, the leaf spring element 25 between the retaining jaws 182.

Furthermore, the two retaining jaws 182 are each provided with two bores 188 oriented perpendicularly to the retaining faces 184. Located opposite each bore 188 of a retaining jaw 182 is a further bore 188 of the other retaining jaw 182, and these are aligned coaxially with each other when the blocking recesses 186 are in engagement with the leaf spring element 25 of the connecting element 18 not shown. A coupling device 190 with interacting first coupling elements 192 in the form of bores 188 and second coupling elements 194 in the form of threads or wires, passing in the shape of closed rings, in each case, through two bores of both retaining jaws 182, serves to fix the retaining jaws 182 temporarily to the intermediate section 24. By appropriate adjustment of a length of the threads 196, the retaining faces 184 can be drawn towards each other into a blocking position in which the side faces 60 and 62 lie against the groove bottoms of the blocking recesses 186 that face each other. In this blocking position, the intermediate section 24 is then temporarily stiffened. To release the surgical device 106, after final positioning of the connecting element 18 at the bone screws 16, the coupling device 190 can be released, for example, by severing the second coupling elements 194.

A surgical device 106 corresponding substantially to the device 106 shown in FIGS. 18 and 19 is shown schematically in FIG. 20. It does, however, differ in the configuration of the coupling device 190', which comprises a first coupling element 192' in the form of a coupling bridge, which engages recesses, not shown, in the retaining jaws 182' and, in a coupling position, may engage these in a latching manner.

A further embodiment of a surgical device 106' which may be used for temporarily stiffening the connecting element 18 or one of the other connecting elements described above is shown schematically in FIG. 21. The surgical device 106' comprises a shaped body 198, which has a cuboidal outer contour and surrounds the intermediate section 24' completely with a positively locking connection. It thus forms a blocking element 200 within the meaning of the claims.

To form the shaped body 198, the intermediate section 24' is enveloped or enclosed with a material which is soluble in liquid. For example, this may be a shaped body 198 made of sugar or salt. The shaped body 198 may also contain a mixture of sugar and salt. Other materials which can be dissolved by a liquid, for example, by water, are also conceivable. The connecting element 18 can then be supplied, for example, after its manufacture with the shaped body 198. After implantation of the connecting element 18, in order to remove the shaped body 198, the connecting element 18 can be flushed with a liquid which dissolves the material of which the shaped body 198 is made. After at least partial, preferably complete dissolution of the material forming the shaped body 198, the connecting element 18 is then movable in the desired manner.

Furthermore, it is conceivable to make the shaped body 198 from a material whose aggregate state is changeable for removal of the device 106. For example, the shaped body 198 may be formed from ice, which melts as a result of a change in temperature, i.e., becomes liquid, and, therefore, releases the leaf spring element 25. Instead of ice, biocompatible plastic materials, which as a result of being heated above their flow temperature also at least release the leaf spring element 25 to the extent that it can be deformed in the desired manner, are also conceivable.

A further variant for formation of the shaped body 198 consists in forming it from a resorbable plastic material which, for example, after manufacture of the connecting element 18, is injection-molded onto the intermediate section 24. After implantation of the connecting element 18, the plastic material can then be resorbed by the patient's body, and after complete resorption of the shaped body 198, the leaf spring element 25 is fully exposed and is deformable under load in the desired manner.

If the shaped body 198 is made from a biocompatible plastic material, it can, for example, also be released from the leaf spring element 25 by ultrasound.

In particular, the device 106', but also the other surgical devices 106 described above, make temporary restriction of the movement of the intermediate section 24 possible. During implantation of the respective connecting element, they protect the intermediate section against any damage. The described surgical devices make it possible to implant the described connecting elements in a neutral position, i.e., free of load.

The connecting elements described in conjunction with the Figures may be made of a metallic material or a plastic material. Examples of suitable materials have been given hereinabove.

What is claimed:

1. A surgical device for temporarily stiffening an at least partially flexible intermediate section of a connecting element for a spinal column stabilization system, said connecting element comprising a first attachment section for fixing to a first bone fixation device, a second attachment section for fixing to a second bone fixation device, and said intermediate section arranged or formed between said first and second attachment sections, said intermediate section defining at least one recess which is configured so as to enable deformation of said intermediate section, said surgical device comprising:
    at least one blocking element which is adapted to be brought into engagement with said intermediate section at least partially with a positively locking connection for temporarily preventing deformation of said intermediate section; and
    at least two cooperating retaining jaws, the at least two cooperating retaining jaws comprising a first retaining jaw and a second retaining jaw, the first retaining jaw comprising a first planar retaining face, and the second retaining jaw comprising a second planar retaining face, the second planar retaining face facing the first planar retaining face,
    the first retaining jaw defining a U-shaped groove as seen normal to the first planar retaining face, the U-shaped groove recessed within the first planar retaining face, the U-shaped groove configured for receiving at least a portion of said intermediate section, the U-shaped groove being defined by a pair of side faces recessed within the first planar retaining face and substantially facing each other, each side face of the U-shaped groove extending substantially perpendicularly to the first planar retaining face.

2. The surgical device of claim 1, wherein the at least one blocking element is configured so as to correspond or substantially correspond to a recess in the intermediate section.

3. The surgical device of claim 1, wherein the at least one blocking element is insertable with a positively locking connection or substantially with a positively locking connection into a recess in the intermediate section.

4. The surgical device of claim 1, wherein the at least two retaining jaws are movable in a direction of movement towards each other and away from each other.

5. The surgical device of claim 4, wherein the at least two retaining jaws comprise a total of at least two axial stops that face each other and are configured so as to act relative to each other in a direction transverse to the direction of movement of the retaining jaws in order to prevent movement of the intermediate section in the axial direction.

6. The surgical device of claim 4, comprising a locking mechanism for preventing movement of the retaining jaws in the direction of movement away from each other in a blocking position.

7. The surgical device of claim 4, wherein at least one of the retaining jaws carries or comprises the at least one blocking element.

8. The surgical device of claim 4, wherein the at least one blocking element is configured in the form of a blocking projection which protrudes from one of the first and second planar retaining faces.

9. The surgical device of claim 8, wherein the blocking projection is in the form of a cylindrical peg or is of wedge-shaped or substantially wedge-shaped configuration.

10. The surgical device of claim 4, wherein the at least one blocking element is configured in the form of a blocking recess provided in one of the first and second planar retaining faces for at least partially receiving the intermediate section to be temporarily stiffened.

11. The surgical device of claim 4, wherein the at least two retaining jaws differ in their configuration.

12. The surgical device of claim 4, comprising a coupling device for releasably connecting the at least two retaining jaws to each other in a coupling position.

13. The surgical device of claim 12, wherein the coupling device comprises first and second coupling elements which are arranged or formed, on the one hand, on the first retaining jaw, and, on the other hand, on the second retaining jaw and are in engagement in the coupling position.

14. The surgical device of claim 12, wherein the coupling device comprises a coupling bridge or a thread.

15. The surgical device of claim 1, comprising an actuating device for transferring the device from an applying position in which the surgical device and the intermediate section are disengaged to a blocking position in which the intermediate section is held by the surgical device in an undeformable or substantially undeformable manner on the surgical device.

16. A spinal column stabilization system comprising at least one first bone fixation device, at least one second bone fixation device and a connecting element, said connecting element comprising a first attachment section for fixing to the at least one first bone fixation device, a second attachment section for fixing to the at least one second bone fixation device, and an at least partially flexible intermediate section arranged or formed between the first and second attachment sections, said intermediate section defining at least one recess which is configured so as to enable deformation of said intermediate section, said spinal column stabilization system further comprising a surgical device for temporarily stiffening said flexible intermediate section of said connecting element, said surgical device comprising at least one blocking element which is adapted to be brought into engagement with said intermediate section at least partially with a positively locking connection for temporarily preventing deformation of said flexible intermediate section, said surgical device further comprising at least two cooperating retaining jaws, the at least two cooperating retaining jaws comprising a first retaining jaw and a second retaining jaw, the first retaining jaw comprising a first planar retaining face, and the second retaining jaw comprising a second planar retaining face the second planar retaining face facing the first planar retaining face, the first retaining jaw defining a U-shaped groove as seen normal to the first planar retaining face, the U-shaped groove recessed within the first planar retaining face, the U-shaped groove configured for receiving at least a portion of said intermediate section, the U-shaped groove being defined by a pair of side faces recessed within the first planar retaining face and substantially facing each other, each side face of the U-shaped groove extending substantially perpendicularly to the first planar retaining face.

17. The spinal column stabilization system of claim 16, wherein the at least one blocking element is insertable at least partially into the at least one recess for temporarily preventing deformation of the intermediate section.

18. The spinal column stabilization system of claim 16, wherein the intermediate section is configured in the form of a strip-shaped, wound leaf spring element and comprises at least one recess which is open at the side in a direction transverse to a longitudinal axis defined by the intermediate section.

* * * * *